(12) United States Patent
Martínez Gil et al.

(10) Patent No.: US 9,604,947 B2
(45) Date of Patent: Mar. 28, 2017

(54) SUBSTITUTED 5-IMINO-1,2,4-THIADIAZOLES THAT CAN BE USED TO TREAT NEURODEGENERATIVE DISEASES

(75) Inventors: Ana Martínez Gil, Madrid (ES); Carmen Gil Ayuso-Gontan, Madrid (ES); Valle Palomo Ruiz, Madrid (ES); Daniel Perez Fernandez, Madrid (ES); Concepción Perez Martín, Madrid (ES); Ana María Perez Castillo, Madrid (ES); María Isabel Loza Garcia, Santiago de Compostela (ES); María Isabel Cadavid Torres, Santiago de Campostela (ES); José Brea Floriani, Santiago de Compostela (ES)

(73) Assignee: CONSEJO SUPERIOR DE INVESTIGACIONES CIENTIFICAS (CSIC), Madrid (ES)

( * ) Notice: Subject to any disclaimer, the term of this patent is extended or adjusted under 35 U.S.C. 154(b) by 544 days.

(21) Appl. No.: 13/499,901

(22) PCT Filed: Oct. 4, 2010

(86) PCT No.: PCT/ES2010/070641
§ 371 (c)(1),
(2), (4) Date: May 21, 2012

(87) PCT Pub. No.: WO2011/039403
PCT Pub. Date: Apr. 7, 2011

(65) Prior Publication Data
US 2012/0225879 A1   Sep. 6, 2012

(30) Foreign Application Priority Data
Oct. 2, 2009 (ES) .................................. 200930787

(51) Int. Cl.
| A61K 31/535 | (2006.01) |
| A01N 43/40 | (2006.01) |
| A61K 31/44 | (2006.01) |
| A61K 31/41 | (2006.01) |
| A01N 43/82 | (2006.01) |
| C07D 285/08 | (2006.01) |
| A61K 31/433 | (2006.01) |

(52) U.S. Cl.
CPC .......... *C07D 285/08* (2013.01); *A61K 31/433* (2013.01)

(58) Field of Classification Search
CPC .............. A61K 31/433; A61K 31/4439; A61K 31/5377; A61P 11/00; A61P 11/06; A61P 17/00; A61P 19/02; A61P 1/00; A61P 21/00; A61P 25/00; A61P 25/14; A61P 25/16; A61P 25/28; A61P 27/02; A61P 27/16; A61P 29/00; A61P 31/00; A61P 37/00

USPC ............... 514/236.2, 342, 361; 544/134; 546/268.7; 548/128
See application file for complete search history.

(56) References Cited

U.S. PATENT DOCUMENTS

| 7,375,123 B2 * | 5/2008 | Eisinger .................. A61K 8/49 514/361 |
| 8,501,791 B2 * | 8/2013 | Eisinger .................. A61K 8/49 514/361 |
| 2003/0162819 A1 * | 8/2003 | Eisinger et al. ............... 514/361 |
| 2003/0176425 A1 * | 9/2003 | Eisinger et al. ........... 514/227.8 |

FOREIGN PATENT DOCUMENTS

| WO | WO-03040117 | 5/2003 |
| WO | WO-2008119057 | 10/2008 |

OTHER PUBLICATIONS

Baker et al. (Gene Therapy, 2003, 10, 844-853, Nature).*
Asif (Int. J of ChemTech Research, 1, 4, 1200-1205, Oct.-Dec. 2009).*
Nieuwendijk et al. (J. Med Chem, 2004, 47, 663-672).*
Brandon, Nicholas J., et al., "Potential CNS Applications for Phosphodiesterase Enzyme Inhibitors", *Annual Reports in Medicinal Chemistry*, vol. 42, (2007), pp. 3-12.
Chetia, J.P. , et al., "One-Pot Synthesis of 2-Aryl-3-phenyl(benzyl)-5-phenylimino-A4-1,2,4-thiadiazolines using N-Chlorosuccinimide", Department of Chemistry, North-Eastern Hill University Shillong; *Comunications*, (Jan. 1985), 2 pages.
Claramunt, Rosa M., et al., "Structural Studies of Two Tinuvin® P Analogs: 2-(2,4-Dimethylphenyl)-2H-benzotriazole and 2-Phenyl-2H-benzotriazole". *Molecules 2007 by MDPI*, (Sep. 21, 2007), pp. 2201-2214.

(Continued)

*Primary Examiner* — Uma Ramachandran
(74) *Attorney, Agent, or Firm* — Blakely Sokoloff Taylor & Zafman LLP

(57) ABSTRACT

The present invention is based on the use of a broad family of 5-imino-1,2,4-thiadiazoles as potential new drugs for the treatment of diseases in which PDE7 inhibition is important, specially inflammatory diseases, autoimmune and neurodegenerative disorders. On the other hand, compounds of the 5-imino-1,2,4-thiadiazole family are here described, as well as their synthetic procedures, and they may have great application as drug or drug candidates.
Therefore, a first aspect of the present invention is related to a compound of formula (I):

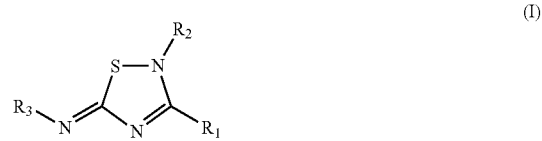

(I)

17 Claims, 4 Drawing Sheets

(56) References Cited

OTHER PUBLICATIONS

Cunico, Robert F., et al., "Palladium-Catalyzed Synthesis of r-Iminoamides from Imidoyl Chlorides and a Carbamoylsilane", *J. Ong. Chem. 2005, 70; JOCNote*, (Mar. 17, 2005), pp. 5344-5346.
Gil, Carmen, et al., "PDE7 Inhibitors as New Drugs for Neurological and Inflammatory Disorders", *Expert Opinion; Informa Healthcare*, (2008), pp. 1127-1139.
Goblyos, Aniko, "Synthesis and Biological Evaluation of a New Series of 2,3,5-Substituted [1,2,4]-Thiadiazoles as Modulators of Adenosine A1 Receptors and Their Molecular Mechanism of Action", *J. Med. Chem.* 2005, 48, (Aug. 11, 2004), pp. 1145-1151.
Kroncke, Klaus-D., et al., "Nitric Oxide: Cytotoxicity versus Cytoprotection—How, Why, When, and Where?", *Nitric Oxide: Biology and Chemistry*; vol. 1, No. 2, (Apr. 1997), pp. 107-120.
Li, Linsong, et al., "CD3- and CD28-Dependent Induction of PDE7 Required for T Cell Activation", *Science 283, 848*, Downloaded from www.sciencemag.org on Mar. 31, 2008, (1999), 5 pages.
Lugnier, Claire, "Cyclic nucleotide phosphodiesterase (PDE) superfamily: A new target for the development of specific therapeutic agents", *Pharmacology & Therapeutics 109*, (2006), pp. 366-398.
Luna-Medina, Rosario, et al., "Regulation of Inflammatory Response in Neural Cells in Vitro by Thiadiazolinones Derivated through Peroxisme Proliferator-activated Receptor y Activation", *The Journal of Biological Chemistry; The American Society for Biochemistry and Molecular Biology, Inc.*, (Apr. 6, 2005), pp. 21453-21462.
Menniti, Frank S., et al., "Phosphodiesterases in the CNS: targets for drug development", www.nature.com/reviews/drugdisc, (Aug. 2006), pp. 660-670.
Nakata, A., "Potential Role of Phosphodiesterase 7 in Human T Cell Function: Comparative Effects of Two Phosphodiesterase Inhibitors", *Clin Exp Immunol 2002*; 128, (Dec. 13, 2002), pp. 460-466.
Perez-Torres, S., et al., "Alterations on Phosphodiesterase Type 7 and 8 Isozyme mRNA Expression in Alzheimer's Disease Brains Examined by in situ Hybridization", *Experimental Neurology 182*, (2003), pp. 322-334.
PCT Search Report and Written Opinion mailed Feb. 22, 2011, PCT Appln. No. PCT/ES2010/070641, with English language translation, 20 pages.
Ambinter (Chemical Library), RN: 1091776-25-8, N-[2-(4-metilfenil)-3-fenil-1,2,4-tiadiazol-5(2H)-iliden-2-propen-1-amina; Available Dec. 30, 2008; Database: Registry [on line] [retrieved on Oct. 21, 2010]; Retrieved from STN International, Columbus, Ohio (EE.UU.), 1 page.
Goblyos, Aniko, et al., "Allosteroc modulation of adenosine receptors", *Purinergic Signalling*, vol. 5, (2009), 51-61.
Goerdeler, J., et al., "Über die Zerfallsprodukte von Imino-delta3-1,2,4-thiadiazolinen", *Chemische Berichte*, vol. 112, (1979), 1288-1296.
Van Den Nieuwendijk, Adrianus M., et al., "Synthesis and Biological Evaluation of 2,3,5-Substituted [1,2,4]Thiadiazoles as Allosteric Modulators of Adenosine Receptors", *J. Med. Chem.*, vol. 47, (2004), 663-672.
Barnikow, G. et al., "Über die oxidative Cyclisierung von Imidoyl-thio-harnstoffen", *Zeitschrift für Chemie* vol. 12, No. 4 1972, p. 130.
Ambinter (Chemical Library), RN: 1091776-25-8, N-[2-(4-metilfenil)-3-fenil-1,2,4-tiadiazol-5(2H)-iliden-2-propen-1-amina; Available Dec. 30, 2008; Database: Registry [on line] [retrieved on Oct. 21, 2010]; Retrieved from STN International, Columbus, Ohio (E.UU.), 1 pages.
Goblyos, Aniko, et al., "Allosteric modulation of adenosine receptors", *Purinergic Signalling*, vol. 5 (2009), 51-61.
Goerdeler, J., et al., "Über die Zerfallsprodukte von Imino-delta3-1,2,4-thiadiazolinen", *Chemische Berichte*, vol. 112, (1979), 1288-1296.
CB 1879426 German Document, pp. 426-429.

\* cited by examiner

SUBSTITUTED 5-IMINO-1,2,4-THIADIAZOLES THAT CAN BE USED TO TREAT NEURODEGENERATIVE DISEASES

CROSS-REFERENCE TO RELATED APPLICATIONS

The present patent application is a national phase application of International Application No. PCT/ES2010/070641, filed Oct. 4, 2010, which application claims priority to Spanish Application No. P 200930787, filed Oct. 2, 2009.

FIELD OF THE INVENTION

The present invention relates to heterocyclic 5-imino-1,2,4-thiadiazoles derivatives and their potential for the treatment of neurodegenerative and/or neurological disorders, as well as diseases with a systemic or central inflammatory component. Therefore, the invention relates to the pharmaceutical sector.

BACKGROUND

The inhibitory activity of phosphodiesterases (PDEs) consists in the degradation of cyclic nucleotides (cAMP and cGMP) by hydrolysis of the 3'-phosphodiester bond, resulting in the inactive compound 5'-monophosphate. cAMP and cGMP are respectively formed by the adenylate cyclase and guanylate cyclase, acting as second messengers in the intracellular signal transduction. A way to increase intracellular levels of cAMP or cGMP is by PDEs inhibition, since they are their unique degradation pathway. The interest of developing specific PDE inhibitors is based on their anti-inflammatory and immunosuppressive properties shown by agents that can raise intracellular levels of cAMP. Therefore, selective cAMP PDE inhibitors may be interesting as a therapy for the treatment of different diseases [Lugnier, C. Cyclic nucleotide phosphodiesterase (PDE) super family: A new target for the development of specific therapeutic agents. *Pharmacol. Ther.* 2006, 109, 366-398], mainly immune system alterations, such as multiple sclerosis, inflammatory and also central nervous system (CNS) disorders [Menniti F. S., Faraci W. S., Schmidt C. J. Phosphodiesterases in the CNS: targets for drug development. *Nat. Rev. Drug Discov.* 2006, 5, 660-670]. Since almost every PDE is expressed in 20CNS, showing in many diseases an increase of function, PDE inhibitors may be also considered as promising drugs for the treatment of psychiatric and neurodegenerative diseases. [Brandon, N. J.; Rotella, D. P. Potencial CNS applications for PDE inhibitors. *Ann. Rep. Med. Chem.* 2007, 42, 3-12].

As an example, cilostazol, a selective PDE3 inhibitor, has shown to reduce cellular death after stroke (cerebral infarct) and also to promote survival in axotomized ganglion cells of retina. Sildenafil, a PDE5 inhibitor, may improve learning by modulation of NO-cGMP signal transduction, a pathway related to cognitive decline due to age in neurodegenerative diseases. On the other hand, selective PDE10A inhibitors are potent antipsychotic agents able to improve the cognition symptoms of schizophrenia and PDE4 inhibitors represent an interesting approach for the treatment in memory disorders. As an example, Memory Pharmaceuticals is developing a PDE4 inhibitor named MEM 414 for the treatment of Alzheimer's disease (http://www.memorypharma.com/p_MEM1414.html, Exp. Neurol. 2003, 182, 322-334).

Among the 11 PDE isoenzymes identified, PDE7 is specific for cAMP, not affected by Rolipram (PDE4 inhibitor), expressed in different brain areas, as well as in lymphocytes. [Li, L.; Yee, C.; Beavo, J. A. CD3- and CD28-dependent induction of PDE7 required for T cell activation. *Science* 1999, 283, 848-851; Nakata, A.; Ogawa, K.; Sasaki, T.; Koyama, N.; Wada, K.; Kotera, J.; Kikkawa, H.; Omori, K.; Kaminuma, O. Potential role of PDE7 in human T cell function: comparative effects of two PDE inhibitors. *Clin. Exp. Immunol.* 2002, 128, 460-466] and its inhibitors have been useful for the study of its physiology and pathology [Martinez, A. PDE7 inhibitors as new drugs for neurological and anti-inflammatory disorders. *Exp. Opin. Ther. Patents* 2008, 18, 1127-1139]. Thus, it has been shown that the PDE7 selective inhibitor BRL-50481 does not decrease T cell proliferation itself, however it increases synergically the effect of the PDE4 inhibitor Rolipram on the raise of cAMP levels. However, new molecules are needed to validate their pharmacological effects both in vitro and in vivo.

Related to PDE7, it has been reported the use of its inhibitors for the treatment of movement disorders as for example Parkinson's disease. These utilities are described on the patent application WO 2008119057 (Omeros Corporation).

BRIEF DESCRIPTION OF DRAWINGS

The FIG. 1 represents the nitrite production in lipopolysaccharide (LPS) stimulated microglia by using different compounds of the present invention at 30 µM The FIG. 2 represents the nitrite production in LPS stimulated microglia by using different compounds of the present invention at 10 µM.

The FIG. 3 represents the nitrite production in LPS stimulated microglia by using different compounds of the present invention at 10 µM or 5 µM.

Figure 4:
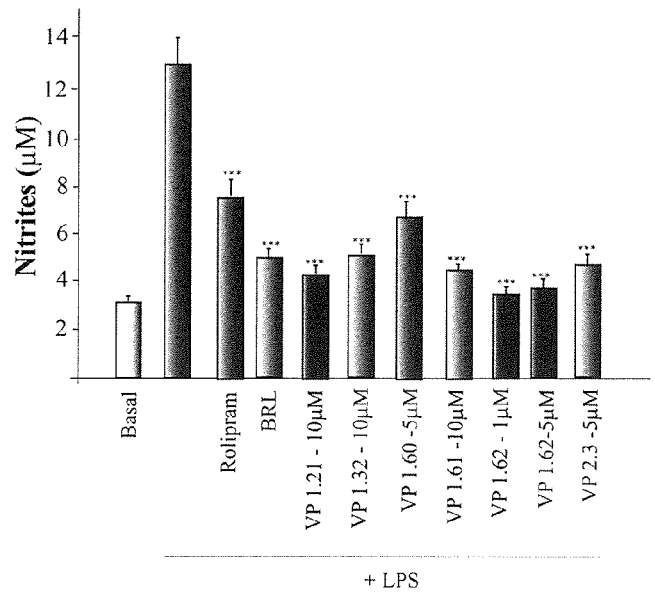

The FIG. 4 represents the nitrite production in LPS stimulated microglia by using different compounds of the present invention at 10 µM, 5 µM or 1 µM.

Figure 5:
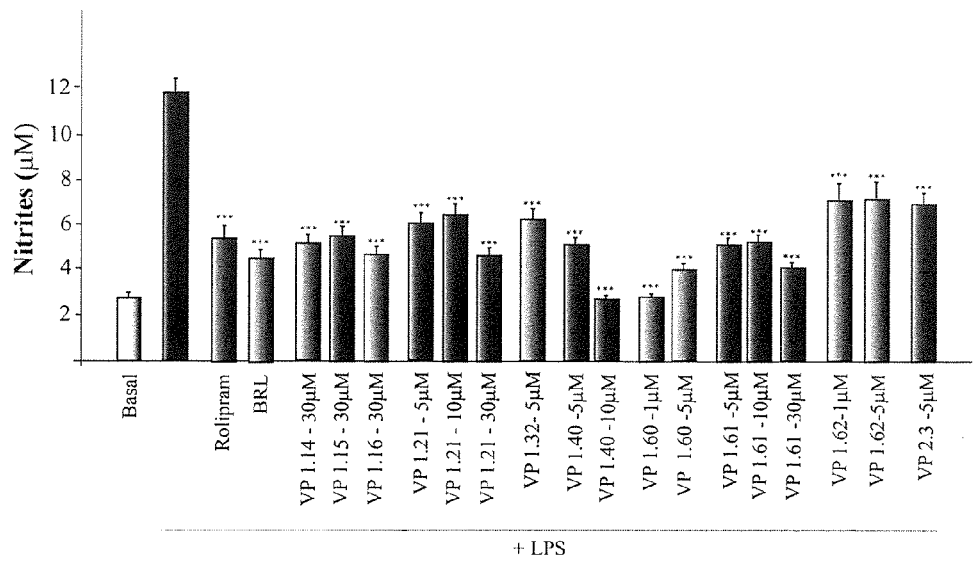

The FIG. 5 represents the nitrite production in LPS stimulated microglia by using different compounds of the present invention at 30 µM, 10 µM, 5 µM or 1 µM.

DETAILED DESCRIPTION OF THE INVENTION

The present invention is based on the use of a broad family of 5-imino-1,2,4-thiadiazoles as potential new drugs for the treatment of neurodegenerative diseases in which PDE7 inhibition is important, specially inflammatory diseases, autoimmune and neurodegenerative disorders. On the other hand, compounds of the 5-imino-1,2,4-thiadiazole family are here described, as well as their synthetic procedures, and they may have great application as drug or drug candidates.

Therefore, a first aspect of the present invention is related to a compound of formula (I):

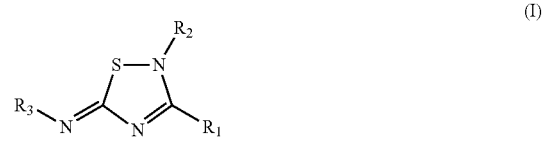

wherein:

$R_1$ is H, CN, $NO_2$, F, Cl, Br, I, or a $X_1$—$R_1'$ group, wherein $X_1$ is a single bond or a group selected from C, $C_1$-$C_6$ alkyl, $C_2$-$C_6$ alkenyl, $C_2$-$C_6$ alkynyl, aryl, heteroaryl, $C_3$-$C_{10}$ cycloalkyl and $C_3$-$C_{10}$ heterocycloalkyl; being $X_1$ optionally substituted with at least one or more groups which may be identical or different and are selected from H, $C_1$-$C_6$ alkyl, $C_2$-$C_6$ alkenyl, $C_2$-$C_6$ alkynyl, $C_3$-$C_{10}$ cycloalkyl, $C_3$-$C_{10}$ heterocycloalkyl, F, Cl, Br, I, —OH, =O, —CN, —$NR_4R_5$, —$NO_2$, —$CO_2R_4$, —C(=O)$NR_4$, —$OR_4$, —$SR_4$, —$SO_2NR_4R_5$ and —$NR_4R_5$;

$R_1'$ is H, $C_1$-$C_6$ alkyl, $C_2$-$C_6$ alkenyl, $C_2$-$C_6$ alkynyl, $C_1$-$C_6$ alkoxy, aryl, heteroaryl, $C_3$-$C_{10}$ cycloalkyl or $C_3$-$C_{10}$ heterocycloalkyl; being $R_1'$ optionally substituted with at least one or more groups $X_1'$—$R_8$ which may be identical or different; being $R_1'$ optionally substituted with at least one or more groups $X_1'$—$R_8$ which may be identical or different;

$X_1$ is a single bond or a group selected from C, $C_1$-$C_6$ alkyl, $C_2$-$C_6$ alkenyl, $C_2$-$C_6$ alkynyl, aryl, heteroaryl, $C_3$-$C_{10}$ cycloalkyl and $C_3$-$C_{10}$ heterocycloalkyl, —C(O)O—, amino, —O—, —S-y-$SO_2$—; being $X_1'$ optionally substituted with at least one or more groups which may be identical or different selected from H, $C_1$-$C_3$ alkyl, $C_2$-$C_6$ alkenyl, $C_2$-$C_6$ alkynyl, $C_4$-$C_6$ cycloalkyl, F, Cl, Br, I, =O, —CN, —$NO_2$, —$CO_2R_4$, —$OR_4$, —$SR_4$, —$SO_2NR_6R_7$, =$NR_4$ and —$NR_6R_7$, wherein $R_6$ and $R_7$ are independently selected from $R_4$ and $R_5$ $R_8$ is H, —OH, =O, —$NO_2$, CN, F, Cl, Br, I, $C_1$-$C_4$ alkyl, —$CO_2R_{6a}$, —C(=O)$R_{6a}$, C(=S)$R_{6a}$, $SO_2R_{6a}$, $SOR_{6a}$, $SO_3R_{6a}$, $SR_{6a}$, $OR_{6a}$, C(=O)$NR_{6a}R_{7a}$, C(=S)$NR_{6a}R_{7a}$, C(=N—CN)$NR_{6a}R_{7a}$, C(=N—$SO_2NH_2$)$NR_{6a}R_{7a}$, C(=CH—$NO_2$)$NR_{6a}R_{7a}$, $SO_2NR_{6a}R_{7a}$, C(=$NR_{6a}$)$NHR_{7a}$, C(=$NR_{6a}$)$R_{7a}$ or $NR_{6a}R_{7a}$, wherein $R_{6a}$ and $R_{7a}$ are independently selected from $R_4$ and $R_5$ $R_2$ is H, $C_1$-$C_6$ alkyl, $C_2$-$C_6$ alkenyl, $C_2$-$C_6$ alkynyl, aryl, heteroaryl, $C_3$-$C_{10}$ cycloalkyl and $C_3$-$C_{10}$ heterocycloalkyl, CN or amino; being $R_2$ optionally substituted with at least one or more groups which may be identical or different selected from H, $C_1$-$C_6$ alkyl, $C_2$-$C_6$ alkenyl, $C_2$-$C_6$ alkynyl, aryl, heteroaryl, $C_3$-$C_{10}$ cycloalkyl and $C_3$-$C_{10}$ heterocycloalkyl, =O, —$NO_2$, CN, F, Cl, Br, I, $C_1$-$C_4$ alkyl, —$CO_2R_{6b}$, —C(=O)$R_{6b}$, $SO_2R_{6b}$, $SOR_{6b}$, $SO_3R_{6b}$, $SR_{6b}$, $OR_{6b}$, C(=O)$NR_{6b}R_{7b}$, $SO_2NR_{6b}R_{7b}$, and $NR_{6b}R_{7b}$, wherein $R_{6b}$ and $R_{7b}$ are independently chosen from $R_4$ and $R_5$;

$R_3$ is H, $C_1$-$C_6$ alkyl, $C_2$-$C_6$ alkenyl, $C_2$-$C_6$ alkynyl, aryl, heteroaryl, $C_3$-$C_{10}$ cycloalkyl and $C_3$-$C_{10}$ heterocycloalkyl; being $R_3$ optionally substituted with at least one or more groups $X_3$—$R_9$ which may be identical or different;

$X_3$ is a single bond or a group selected from $C_1$-$C_6$ alkyl, $C_2$-$C_6$ alkenyl, $C_2$-$C_6$ alkynyl, aryl, heteroaryl, $C_3$-$C_{10}$ cycloalkyl and $C_3$-$C_{10}$ heterocycloalkyl, —C(O)O—, amino, —O—, —S-y-$SO_2$—; being $X_3$ optionally substituted with at least one or more groups which may be identical or different selected from H, $C_1$-$C_3$ alkyl, $C_1$-$C_6$ alkyl, $C_2$-$C_6$ alkenyl, $C_2$-$C_6$ alkynyl, $C_3$-$C_{10}$ cycloalkyl, F, Cl, Br, I, =O, —CN, —$NO_2$, —$CO_2R_{6c}$, —$OR_{6c}$, —$SR_{6c}$, —$SO_2NR_{6c}R_{7c}$, =$NR_{6c}$ and —$NR_{6c}R_{7c}$ being $R_{6c}$ and $R_{7c}$ independently chosen from $R_4$ and $R_5$ $R_9$ is H, —OH, =O, —$NO_2$, CN, F, Cl, Br, I, $C_1$-$C_4$ alkyl, $C_2$-$C_6$ alkenyl, $C_2$-$C_6$ alkynyl, aryl, heteroaryl, $C_3$-$C_{10}$ cycloalkyl y $C_3$-$C_{10}$ heterocycloalkyl, —$CO_2R_4$, —C(=O) $R_{6d}$, $SO_2R_{6d}$, $SOR_{6d}$, $SO_3R_{6d}$, $SR_{6d}$, $OR_{6d}$, C(=O) $NR_{6d}R_{7d}$, $SO_2NR_{6d}R_{7d}$, C(=$NR_{6d}$)$NHR_{7d}$, C(=$NR_{6d}$)$R_{7d}$ or $NR_{6d}R_{7d}$, being $R_{6d}$ and $R_{7d}$, $R_{7c}$ independently chosen from $R_4$ and $R_5$;

$R_4$ and $R_5$ are independently selected from: H, $C_1$-$C_6$ alkyl $C_2$-$C_6$ alkenyl, $C_2$-$C_6$ alkynyl, $C_3$-$C_7$ $X_4$-cycloalkyl, $X_4$-cyclobutyl, $X_4$-cyclopentyl, $X_4$-cyclohexyl, $X_4$-cycloheptyl, $X_4$-benzyl, $X_4$-pyridinyl, $X_4$-pyrimidinyl, $X_4$-piperidinyl, $X_4$-pyrrolidinyl, $X_4$-pyrrolyl, $X_4$-imidazolyl and $X_4$-pyranyl saturated or unsaturated; being optionally substituted the groups $R_4$ and $R_5$ with one or more groups selected from =O, —$NO_2$, CN, F, Cl, Br, I, $C_1$-$C_4$ alkyl, —$CO_2R_{10}$, —C(=O)$R_{10}$, C(=S)$R_{10}$, $SO_2R_{10}$, $SOR_{10}$, $SO_3R_{10}$, $SR_{10}$, $OR_{10}$, C(=O)$NR_{10}R_{11}$, C(=N—$SO_2NH_2$)$NR_{10}R_{11}$, C(=CH—$NO_2$)$NR_{10}R_{11}$, $SO_2NR_{10}R_{11}$, C(=$NR_{10}$)$NHR_{11}$, C(=$NR_{10}$)$R_{11}$ and $NR_{10}R_{11}$;

$X_4$ is a single bond or a group selected from $C_1$-$C_6$ alkyl, $C_2$-$C_6$ alkenyl; each one of the groups optionally substituted with one or more groups that can be identical or different and are selected from =O, —$NO_2$, CN, F, Cl, Br, I, $C_1$-$C_3$ alkyl, —$CO_2R_{10}$, —C(=O)$R_{10}$, $OR_{10}$, C(=O)$NR_{10}R_{11}$, —$SO_2NR_{10}R_{11}$ and $NR_{10}R_{11}$; and $R_{10}$ and $R_{11}$ are independently selected from H and $C_1$-$C_6$ alkyl.

Preferably, the present invention relates to compounds of general formula (I), wherein: $R_3$ is H, C, $C_1$-$C_6$ alkyl, $C_2$-$C_6$ alkenyl, $C_2$-$C_6$ alkynyl, $C_3$-$C_7$ cycloalkyl, cyclobutyl, cyclopentyl, cyclohexyl, cycloheptyl, phenyl, naphthyl, pyridinyl, pyrimidinyl, piperidinyl, pyrrolidinyl, pyrrolyl, imidazolyl or pyranyl; being $R_3$ optionally substituted with at least one or more groups $X_3$—$R_9$ which may be identical or different; $X_3$ is a group selected from C, $C_1$-$C_6$ alkyl, $C_2$-$C_6$ alkenyl, $C_2$-$C_6$ alkynyl, $C_3$-$C_7$ cycloalkyl, phenyl, naphthyl, pyridinyl, pyrimidinyl, piperidinyl, pyrrolidinyl, pyrrolyl, imidazolyl, pyranyl, —C(O)O—, amino, —O—, —S— and —$SO_2$—; being $X_3$ optionally substituted with at least one or more groups which may be identical or different selected from H, $C_1$-$C_3$ alkyl, $C_2$-$C_6$ alkenyl, $C_2$-$C_6$ alkynyl, $C_4$-$C_7$ cycloalkyl, F, Cl, Br, I, =O, —CN, —$NO_2$, —$CO_2R_{6c}$, —$OR_{6c}$, —$SR_{6c}$, —$SO_2NR_{6c}R_{7c}$, =$NR_{6c}$ and —$NR_{6c}R_{7c}$, being $R_{6c}$ and $R_{7c}$ independently selected from $R_4$ and $R_5$; and $R_9$ is H, —OH, =O, —$NO_2$, —CN, F, Cl, Br, I, $C_1$-$C_3$ alkyl, —C(=O)$R_{6d}$, $SR_{6d}$, $OR_{6d}$, C(=O)$NR_{6d}R_{7d}$ or $NR_{6d}R_{7d}$, being $R_{6d}$ and $R_{7d}$ independently selected from $R_4$ and $R_5$.

Preferably for the present invention, $R_3$ is $C_1$-$C_6$ alkyl, being $R_3$ optionally substituted with at least one or more groups $X_3$—$R_9$ which may be identical or different; $X_3$ is a group selected from $C_3$-$C_7$ cycloalkyl, phenyl, naphthyl, pyridinyl, pyrimidinyl, piperidinyl, pyrrolidinyl, pyrrolyl o imidazolyl; being $X_3$ optionally substituted with at least one or more groups which may be identical or different and are selected from H, $C_1$-$C_3$ alkyl, $C_2$-$C_6$ alkenyl, $C_2$-$C_6$ alkynyl, $C_4$-$C_7$ cycloalkyl, F, Cl, Br, I, =O, —CN, —$NO_2$, —$CO_2R_{6c}$, —$OR_{6c}$, —$SR_{6c}$, —$SO_2NR_{6c}R_{7c}$, =$NR_{6c}$ and —$NR_{6c}R_{7c}$, being $R_{6c}$ and $R_{7c}$ independently selected from $R_4$ and $R_5$; and $R_9$ is H, —OH, =O, —$NO_2$, —CN, F, Cl, Br, I, $C_1$-$C_3$ alkyl, —C(=O)$R_{6d}$, $SR_{6d}$, $OR_{6d}$, C(=O) $NR_{6d}R_{7d}$ or $NR_{6d}R_{7d}$, being $R_{6d}$ and $R_{7d}$ independently selected from $R_4$ and $R_5$.

Even more preferably, $R_3$ is —$CH_2$—$X_3$—$R_9$. More preferably $X_3$ is pyridinyl; being $X_3$ optionally substituted with at least one or more groups which may be identical or different and are selected from H, $C_1$-$C_3$ alkyl, $C_2$-$C_6$ alkenyl, $C_2$-$C_6$ alkynyl, $C_4$-$C_7$ cycloalkyl, F, Cl, Br, I, =O, —CN, —$NO_2$, —$CO_2R_{6c}$, —$OR_{6c}$, —$SR_{6c}$, —$SO_2NR_{6c}R_{7c}$, and —$NR_{6c}R_{7c}$, being $R_{6c}$ and $R_{7c}$ independently selected from $R_4$ and $R_5$; and $R_9$ is H, —OH, =O, —$NO_2$, —CN, F, Cl, Br, I, $C_1$-$C_3$ alkyl, —C(=O)$R_{6d}$, $SR_{6d}$, $OR_{6d}$, C(=O)$NR_{6d}R_{7d}$, or $NR_{6d}R_{7d}$, being $R_{6d}$ and $R_{7d}$ independently selected from $R_4$ and $R_5$.

Even more preferably for the present invention, $R_4$ and $R_5$ are independently selected from: H, $C_1$-$C_6$ alkyl, $C_2$-$C_6$ alkenyl, $C_2$-$C_6$ alkynyl, $C_3$-$C_7$ $X_4$-cycloalkyl, $X_4$-cyclobutyl, $X_4$-cyclopentyl, $X_4$-cyclohexyl, $X_4'$ cycloheptyl, $X_4$-bencyl, $X_4$-pyridinyl, $X_4$-pyrimidinyl, $X_4$-piperidinyl, $X_4'$ pyrrolidinyl, $X_4$-pyrrolyl and $X_4$-imidazolyl; being optionally substituted the groups $R_4$ and $R_5$ with one or several groups selected from =O, —$NO_2$, CN, F, Cl, Br, I, $C_1$-$C_4$ alkyl, —$CO_2R_{10}$, —C(=O)$R_{10}$, C(=S)$R_{10}$, $SO_2R_{10}$, $SOR_{10}$, $SO_3R_{10}$, $SR_{10}$, $OR_{10}$, C(=O)$NR_{10}R_{11}$, $SO_2NR_{10}R_{11}$, and $NR_{10}R_{11}$; and $X_4$ is a single bond.

Preferably for the present invention, $R_1$ is H, or a group $X_1$—$R_1'$ wherein $X_1$ is a single bond; $R_1'$ is H, $C_1$-$C_6$ alkyl, $C_2$-$C_6$ alkenyl, $C_2$-$C_6$ alkynyl, $C_3$-$C_7$ cycloalkyl, phenyl, naphthyl, pyridinyl, pyrimidinyl, piperidinyl, pyrrolidinyl, pyrrolyl or imidazolyl; being $R_1'$ optionally substituted with one or more groups $X_1'$—$R_8$ which may be identical or different; $X_1'$ is a single bond selected from C, $C_1$-$C_6$ alkyl, $C_2$-$C_6$ alkenyl, $C_2$-$C_6$ alkynyl, $C_3$-$C_7$ cycloalkyl, phenyl, naphthyl, pyridinyl, pyrimidinyl, piperidinyl, pyrrolidinyl, pyrrolyl, imidazolyl, —C(O)O—, amino, —O—, —S— and —$SO_2$—; being $X_1'$ optionally substituted with at least one or more groups which may be identical or different and are selected from H, $C_1$-$C_3$ alkyl, $C_2$-$C_6$ alkenyl, $C_2$-$C_6$ alkynyl, $C_4$-$C_6$ cycloalkyl, F, Cl, Br, I, =O, —CN, —$NO_2$, —$CO_2R_4$, —$OR_4$, —$SR_4$, —$SO_2NR_6R_7$, =$NR_4$ and —$NR_6R_7$, being $R_6$ y $R_7$ independently selected from $R_4$ and $R_5$; and $R_8$; is H, —OH, =O, —$NO_2$, CN, F, Cl, Br, I, $C_1$-$C_3$ alkyl, —$CO_2R_{6a}$, —C(=O)$R_{6a}$, $SO_2R_{6a}$, $SOR_{6a}$, $SO_3R_{6a}$, $SR_{6a}$, $OR_{6a}$, C(=O)$NR_{6a}R_{7a}$, $SO_2NR_{6a}R_{7a}$, C(=$NR_{6a}$)$NHR_{7a}$ or $NR_{6a}R_{7a}$, being $R_{6a}$ and $R_{7a}$ independently selected from $R_4$ and $R_5$.

Preferably for the present invention, $R_1$ is a group $X_1$—$R_1'$ wherein $X_1$ is a single bond; $R_1'$ is aryl or heteroaryl, preferably phenyl, naphthyl, pyridinyl, pyrimidinyl, piperidinyl, pyrrolidinyl, pyrrolyl or imidazolyl; being $R_1'$ optionally substituted with one or more groups $X_1'$—$R_8$ which may be identical or different; $X_1'$ is a single bond or a group selected from C, $C_1$-$C_6$ alkyl, $C_2$-$C_6$ alkenyl, $C_2$-$C_6$ alkynyl, $C_3$-$C_7$ cycloalkyl, phenyl, naphthyl, pyridinyl, pyrimidinyl, piperidinyl, pyrrolidinyl, pyrrolyl, imidazolyl, —C(O)O—, amino, —O—, —S— and —$SO_2$—; being $X_1'$ optionally substituted with at least one or more groups which may be identical or different and are selected from H, $C_1$-$C_3$ alkyl, $C_2$-$C_6$ alkenyl, $C_2$-$C_6$ alkynyl, $C_4$-$C_6$ cycloalkyl, F, Cl, Br, I, =O, —CN, —$NO_2$, —$CO_2R_4$, —$OR_4$, —$SR_4$, —$SO_2NR_6R_7$ and —$NR_6R_7$, being $R_6$ and $R_7$ independently selected from $R_4$ and $R_5$; and $R_8$ is H, —OH, =O, —$NO_2$, CN, F, Cl, Br, I, $C_1$-$C_3$ alkyl, —$CO_2R_{6a}$, —C(=O)$R_{6a}$, $SO_2R_{6a}$, $SOR_{6a}$, $SO_3R_{6a}$, $SR_{6a}$, $OR_{6a}$, C(=O)$NR_{6a}R_{7a}$, $SO_2NR_{6a}R_{7a}$ or $NR_{6a}R_{7a}$, being $R_{6a}$ and $R_{7a}$ independently selected from $R_4$ y $R_5$.

More preferably for the present invention, $R_1$ is a group $X_1$—$R_1'$ wherein $X_1$ is a single bond; $R_1'$ is phenyl, naphthyl, pyridinyl, pyrimidinyl, piperidinyl, pyrrolidinyl, pyrrolyl or imidazolyl; being $R_1'$ optionally substituted with one or more groups $X_1'$—$R_8$ which may be identical or different; $X_1'$ is a single bond or a group selected from C, $C_1$-$C_6$ alkyl, $C_2$-$C_6$ alkenyl, $C_2$-$C_6$ alkynyl, $C_3$-$C_7$ cycloalkyl, phenyl, naphthyl, pyridinyl, pyrimidinyl, piperidinyl, pyrrolidinyl, pyrrolyl, imidazolyl, —C(O)O—, amino, —O—, —S— and —$SO_2$—; being $X_1'$ optionally substituted with at least one or more groups which may be identical or different and are selected from H, $C_1$-$C_3$ alkyl, $C_2$-$C_6$ alkenyl, $C_2$-$C_6$ alkynyl, $C_4$-$C_6$ cycloalkyl, F, Cl, Br, I, =O, —CN, —$NO_2$, —$CO_2R_4$, —$OR_4$, —$SR_4$, —$SO_2NR_6R_7$ and —$NR_6R_7$, being $R_6$ and $R_7$ independently selected from $R_4$ and $R_5$; and $R_8$ is H, —OH, =O, —$NO_2$, CN, F, Cl, Br, I, $C_1$-$C_3$ alkyl, —$CO_2R_{6a}$, —C(=O)$R_{6a}$, $SO_2R_{6a}$, $SOR_{6a}$, $SO_3R_{6a}$, $SR_{6a}$, $OR_{6a}$, C(=O)$NR_{6a}R_{7a}$, $SO_2NR_{6a}R_{7a}$, C(=$NR_{6a}$)$NHR_{7a}$, C(=$NR_{6a}$)$R_{7a}$ or $NR_{6a}R_{7a}$, being $R_{6a}$ and $R_{7a}$ independently selected from $R_4$ and $R_5$.

Even more preferably for the present invention, $R_1$ is a group $X_1$—$R_1'$ wherein $X_1$ is a single bond; $R_1'$ is phenyl, naphthyl, pyridinyl, pyrimidinyl, piperidinyl, pyrrolidinyl, pyrrolyl o imidazolyl; being $R_1'$ optionally substituted with one or more groups $X_1'$—$R_8$ which may be identical or different; $X_1'$ is a single bond; $R_3$ is H, —OH, —$NO_2$, CN, F, Cl, Br, I, $C_1$-$C_3$ alkyl, —$CO_2R_{6a}$, —C(=O)$R_{6a}$, $SO_2R_{6a}$, $SOR_{6a}$, $SO_3R_{6a}$, $SR_{6a}$, $OR_{6a}$, C(=O)$NR_{6a}R_{7a}$, $SO_2NR_{6a}R_{7a}$ or $NR_{6a}R_{7a}$, being $R_{6a}$ and $R_{7a}$ independently selected from $R_4$ and $R_5$.

More preferably for the present invention, $R_1$ is a group $X_1$—$R_1'$ wherein $X_1$ is a single bond; $R_1'$ is phenyl; being $R_1'$ optionally substituted with one or more groups $X_1'$—$R_8$ which may be identical or different; $X_1'$ is a single bond; and $R_8$ is H, —OH, —$NO_2$, CN, F, Cl, Br, I, $C_1$-$C_3$ alkyl, —$CO_2R_{6a}$, —C(=O)$R_{6a}$, $SO_2R_{6a}$, $SOR_{6a}$, $SO_3R_{6a}$, $SR_{6a}$, $OR_{6a}$, C(=O)$NR_{6a}R_{7a}$, $SO_2NR_{6a}R_{7a}$ or $NR_{6a}R_{7a}$, being $R_{6a}$ and $R_{7a}$ independently selected from $R_4$ and $R_5$.

Even more preferably for the present invention, $R_4$ and $R_5$ are independently selected from: H, $C_1$-$C_6$ alkyl, $C_2$-$C_6$ alkenyl, $C_2$-$C_6$ alkynyl, $C_3$-$C_7$ $X_4$-cycloalkyl, $X_4$-cyclobutyl, $X_4$-cyclopentyl, $X_4$-cyclohexyl, $X_4$-cycloheptyl, $X_4$-bencyl, $X_4$-pyridinyl, $X_4$-pyrimidinyl, $X_4$-piperidinyl, $X_4$-pyrrolidinyl, $X_4$-pyrrolyl and $X_4$-imidazolyl; being optionally substituted the groups $R_4$ and $R_5$ with one or more groups selected from =O, —$NO_2$, CN, F, Cl, Br, I, $C_1$-$C_4$ alkyl, —$CO_2R_{10}$, —C(=O)$R_{10}$, C(=S)$R_{10}$, $SO_2R_{10}$, $SOR_{10}$, $SO_3R_{10}$, $SR_{10}$, $OR_{10}$, C(=O)$NR_{10}R_{11}$, $SO_2NR_{10}R_{11}$ and $NR_{10}R_{11}$; and $X_4$ is a single bond.

In another preferred embodiment, $R_2$ is $C_3$-$C_7$ cycloalkyl, phenyl, naphthyl, pyridinyl, pyrimidinyl, piperidinyl, pyrrolidinyl, pyrrolyl or imidazolyl; being $R_2$ optionally substituted with at least one or more groups which may be identical or different and are selected from H, $C_1$-$C_6$ alkyl, $C_2$-$C_6$ alkenyl, $C_2$-$C_6$ alkynyl, aryl, heteroaryl, $C_3$-$C_{10}$ cycloalkyl and $C_3$-$C_{10}$ heterocycloalkyl, F, Cl, Br, I, =O, —$NO_2$, CN, —$CO_2R_{6b}$, —C(=O)$R_{6b}$, $SO_2R_{6b}$, $SOR_{6b}$, $SO_3R_{6b}$, $SR_{6b}$, $OR_{6b}$, C(=O)$NR_{6b}R_{7b}$, $SO_2NR_{6b}R_{7b}$, and $NR_{6b}R_{7b}$, being $R_{6b}$ and $R_{7b}$ independently selected from $R_4$ and $R_5$.

In another preferred embodiment, $R_2$ is $C_3$-$C_7$ cycloalkyl, phenyl, naphthyl, pyridinyl, pyrimidinyl, piperidinyl, pyrrolidinyl, pyrrolyl or imidazolyl; being $R_2$ optionally substituted with at least one or more groups which may be identical or different and are selected from H, $C_1$-$C_6$ alkyl, $C_2$-$C_6$ alkenyl, $C_2$-$C_6$ alkynyl, $C_3$-$C_7$ cycloalkyl, phenyl, naphthyl, pyridinyl, pyrimidinyl, piperidinyl, pyrrolidinyl, pyrrolyl, imidazolyl, F, Cl, Br, I, =O, —$NO_2$, CN, —$CO_2R_{6b}$, —C(=O)$R_{6b}$, $SO_2R_{6b}$, $SOR_{6b}$, $SO_3R_{6b}$, $SR_{6b}$, $OR_{6b}$, C(=O)$NR_{6b}R_{7b}$, $SO_2NR_{6b}R_{7b}$, and $NR_{6b}R_{7b}$, being $R_{6b}$ and $R_{7b}$ independently selected from $R_4$ and $R_5$.

Even more preferably for the present invention, $R_2$ is phenyl; being $R_2$ optionally substituted with at least one or more groups which may be identical or different and are selected from H, $C_1$-$C_6$ alkyl, $C_2$-$C_6$ alkenyl, $C_2$-$C_6$ alkynyl, $C_3$-$C_7$ cycloalkyl, phenyl, naphthyl, pyridinyl, pyrimidinyl, piperidinyl, pyrrolidinyl, pyrrolyl, imidazolyl, F, Cl, Br, I, =O, —$NO_2$, CN, —$CO_2R_{6b}$, —C(=O)$R_{6b}$, $SO_2R_{6b}$, $SOR_{6b}$, $SO_3R_{6b}$, $SR_{6b}$, $OR_{6b}$, C(=O)$NR_{6b}R_{7b}$, $SO_2NR_{6b}R_{7b}$, and $NR_{6b}R_{7b}$, being $R_{6b}$ and $R_{7b}$ independently selected from $R_4$ and $R_5$.

Even more preferably for the present invention, $R_4$ and $R_5$ are independently selected from: H, $C_1$-$C_6$ alkyl, $C_2$-$C_6$ alkenyl, $C_2$-$C_6$ alkynyl, $C_3$-$C_7$ $X_4$-cycloalkyl, $X_4$-cyclobutyl, $X_4$-cyclopentyl, $X_4$-cyclohexyl, $X_4$-cycloheptyl, $X_4$-benzyl, $X_4$-pyridinyl, $X_4$-pyrimidinyl, $X_4$-piperidinyl, $X_4$-pyrrolidinyl, $X_4$-pyrrolyl y $X_4$-imidazolyl: being optionally substituted the groups $R_4$ and $R_5$ with one or more groups selected from =O, —NO$_2$, CN, F, Cl, Br, I, $C_1$-$C_4$ alkyl, —CO$_2$R$_{10}$, —C(=O)R$_{10}$, C(=S)R$_{10}$, SO$_2$R$_{10}$, SOR$_{10}$, SO$_3$R$_{10}$, SR$_{10}$, OR$_{10}$, C(=O)NR$_{10}$R$_{11}$, SO$_2$NR$_{10}$R$_{11}$ and NR$_{10}$R$_{11}$; and $X_4$ is a single bond.

In another preferred embodiment, the invention relates to compounds of formula (I) as a pharmaceutically acceptable salt, but preferably as hydrobromide or hydrochloride salts.

Another aspect of the present invention relates to a compound of general formula (II):

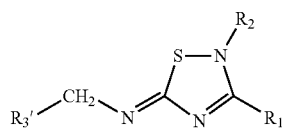

(II)

wherein:

$R_1$ and $R_2$ are as described above;

$R_3'$ is selected from $C_4$-$C_6$ alkyl, $C_2$-$C_6$ alkenyl, $C_2$-$C_6$ alkynyl, heteroaryl, $C_3$-$C_{10}$ cycloalkyl y $C_3$-$C_{10}$ heterocycloalkyl, (CH$_2$)$_n$—(C$_3$-$C_{10}$ heterocycloalkyl), (CH$_2$)$_n$—CN, (CH$_2$)$_n$—OR$_{12}$, (CH$_2$)$_n$—C(O)OR$_{12}$, and (CH$_2$)$_n$—NR$_6{}_f$R$_7{}_f$ being R$_6{}_f$ and R$_7{}_f$ independently selected from $R_4$ and $R_5$ and n is a number between 0 and 20; being $R_3'$ optionally substituted with at least one or more groups which may be identical or different and are selected from, $C_1$-$C_6$ alkyl, $C_2$-$C_6$ alkenyl, $C_2$-$C_6$ alkynyl, aryl, heteroaryl, $C_3$-$C_{10}$ cycloalkyl and $C_3$-$C_{10}$ heterocycloalkyl, =O, —NO$_2$, CN, F, Cl, Br, I, $C_1$-$C_4$ alkyl, —CO$_2$R$_{6e}$, —C(=O)R$_{6e}$, SO$_2$R$_{6e}$, SOR$_{6e}$, SO$_3$R$_{6e}$, SR$_{6e}$, OR$_{6e}$, C(=O)NR$_{6e}$R$_{7e}$, SO$_2$NR$_{6e}$R$_{7e}$, and NR$_{6e}$R$_{7e}$, being R$_{6e}$ and R$_{7e}$ independently selected from $R_4$ and $R_5$.

$R_{12}$ is selected independently from the groups defined for $R_{10}$; and $R_4$ and $R_5$ have been defined before;

Preferably for the compound with general formula (II), $R_3'$ is heteroaryl, —C(O)OR$_{12}$ or —(CH$_2$)$_n$—OR$_{12}$.

Another preferred groups are wherein $R_3'$ is a group —(CH$_2$)$_n$—OR$_{6e}$ being n between 1 and 20, on the condition that $R_3'$ cannot be (CH$_2$)$_2$—OH.

The compound of general formula (II) may be selected of the following compounds:

2,3-Diphenyl-5-(3-pyridylmethylimino)-2,5-dihydro-1,2,4-thiadiazole 3-(4-Methoxyphenyl)-2-phenyl-5-(3-pyridylmethylimino)-2,5-dihydro-1,2,4-thiadiazole 2-(4-Methoxyphenyl)-3-phenyl-5-(3-pyridylmethylimino)-2,5-dihydro-1,2,4-thiadiazole 5-Ethoxycarbonylmethylimino-2,3-diphenyl-2,5-dihydro-1,2,4-thiadiazole 5-Ethoxycarbonylmethylimino-3-(4-methoxyphenyl)-2-phenyl-2,5-dihydro-1,2,4-thiadiazole, 5-Ethoxycarbonylmethylimino-2-(4-methoxyphenyl)-3-phenyl-2,5-dihydro-1,2,4-thiadiazole, 5-(2-Hydroxyethylimino)-2,3-diphenyl-2,5-dihydro-1,2,4-thiadiazole 5-(2-Hydroxyethylimino)-3-(4-methoxyphenyl)-2-phenyl-2,5-dihydro-1,2,4-thiadiazole and 5-(2-Hydroxyethylimino)-2-(4-methoxyphenyl)-3-phenyl-2,5-dihydro-1,2,4-thiadiazole Another aspect of the present invention is related to a pharmaceutically acceptable salt of any of the compounds of general formula (I), more preferably for the ones of general formula (II), and even more preferably as hydrochloride or hydrobromide salts thereof.

Another aspect of the present invention is related to the compound of general formula (I), more preferably to the compound of general formula (II), for its use as a medicament.

Another aspect of the present invention is related to the use of the compound of general formula (I) or to the compound of general formula (II), for the preparation of a drug for the treatment or prevention of inflammatory pathologies, autoimmune, neurodegenerative, neurological disorders, and/or movement disorders, these and other pathologies wherein PDE7 is relevant.

Preferably, the inflammatory and/or autoimmune pathology can be selected from the following group that comprises inflammatory bowel disease, inflammatory joint diseases, atopic dermatitis and other inflammatory dermatological diseases, neuritis, encephalitis, encephalomyelitis and inflammatory diseases that affect the central nervous system (multiple sclerosis) or peripheral nervous system, myositis, vasculitis, systemic lupus erythematosus, asthma, chronic obstructive pulmonary disease, infectious diseases that occur with inflammation, graft rejection, conjunctivitis and inflammatory eye diseases, otitis and mucositis.

Preferably, neurodegenerative or neurological pathologies may be selected from the group that comprises Alzheimer's disease, Parkinson's disease, amyotrophic lateral sclerosis, cerebral ischemia, post-encephalic parkinsonism, dystonias, Tourette's syndrome, periodic limbic movement disorders, restless leg syndrome and attention deficit hyperactivity disorder.

Another aspect of the present invention is related to a pharmaceutical composition that comprises any of the compounds of general formula (I), or any of the compounds of general formula (II), and at least one pharmaceutically acceptable excipient.

DEFINITIONS

The term "alkyl" comprises preferably branched and non branched alkyls as for example methyl, ethyl, n-propyl, iso-propyl, n-butyl, iso-butyl, tert-butyl, sec-butyl, pentyl, iso-pentyl, hexyl, heptyl, octyl, nonyl and decyl and their corresponding isomers.

The term "alkoxy" comprises preferably branched and non branched alkoxides as for example methoxy, ethoxy, propyloxy, iso-propyloxy, butyloxy, iso-butyloxy, tert-butyloxy, sec-butyloxy, pentyloxy, Iso-pentyloxy, hexyloxy, heptyloxy, octyloxy, nonyloxy, decyloxy, undecyloxy and dodecyloxy and their corresponding isomers.

The term "cycloalkyl" comprises preferably a group $C_3$-$C_{10}$, cycloalkyl, more particularly a saturated cycloalkyl group saturated with the length indicated in the ring, as for example; cyclopropyl, cyclobutyl, cyclopentyl, cyclohexyl, cycloheptyl, cyclooctyl, cyclononyl, or cyclodecyl and also comprises unsaturated cycloalkyls that contain one or more double bonds in the carbonated chain as for example cycloalkenyl groups $C_3$-$C_{10}$ such as cyclopropenyl, cyclobutenyl, cyclopentenyl, cyclohexenyl, cycloheptenyl, cyclooctenyl, cyclononenyl, or cyclodecenyl.

Related to the bonds, for the rest of the molecule, the cycloalkyl group may contain single or double bonds, in other words, it may be saturated or unsaturated and may optionally be substituted with one or more times, independently from the other groups with an alkyl group $C_1$-$C_6$ and/or an halogen and/or an $OR^f$ group and/or a $NR^{g1}R^{g2}$ group as for example 2-methylcyclopropyl, 2,2-dimethylcyclopropyl, 2,2-dimethylcyclobutyl, 3-hydroxycyclopentyl, 3-hydroxycyclohexyl, 3-dimethylaminocyclobutyl, 3-dimethylaminocyclopentyl and 4-dimethylaminocyclohexyl groups.

The term "heterocycloalkyl" comprises preferably a cycloalkyl group $C_3$-$C_{10}$, defined before, wherein one of the atoms of the rings is an heteroatom like NH, $NR^{d3}$, O, S or groups like C(O), S(O), S(O)$_2$, or also a group $C_n$-cyclo alkyl (wherein n is a number selected from 3, 4, 5, 6, 7, 8, 9 and 10) wherein one or more of the carbon atoms are substituted by the heteroatoms or before cited groups in order to be a $C_n$-cycloheteroalkyl group; they also comprises unsaturated cycloheteroalkyl groups that contain one or more double bonds in the carbonated chain, therefore related to the bonds, for the rest of the molecule, cycloheteroalkyl group may contain single and double bonds, in other words, it may be saturated or unsaturated and may optionally substituted one or more times, independently of the other groups with an alkyl group $C_1$-$C_6$ and/or an halogen and/or an $OR^f$ group and/or a group.

In this way, the $C_n$-cycloheteroalkyl group is related for example to heterocycles of three members expressed as $C_3$-heterocycloalkyl named Oxyranyles.

Other heterocycloalkyl' examples are oxetanyl ($C_4$), azirydinyl ($C_3$), azetydinyl ($C_4$), tetrahydrofuranyl ($C_5$), pyrrolidinyl ($C_5$), morpholinyl ($C_6$), dithianyl ($C_6$), thiomorpholinyl ($C_6$), piperidinyl ($C_6$), tetrahydropyranyl ($C_6$), piperazinyl ($C_6$), tritianyl ($C_6$), homomorpholinyl ($C_7$), homopiperazinyl ($C_7$) and chinuclydinyl ($C_8$). Examples to the cycloheteroalkyl groups cited before are the compounds, 4-methylpiperazinyl, 3-methyl-4-methylpiperazine, 3-fluoro-4-methylpiperazine, 4-dimethylaminopiperidinyl, 4-methylaminopiperidinyl, 4-aminopiperidinyl, 3-dimethylaminopiperidinyl, 3-methylaminopiperidinyl, 3-aminopiperidinyl, 4-hydroxypiperidinyl, 3-hydroxypiperidinyl, 2-hydroxypiperidinyl, 4-methylpiperidinyl, 3-methylpiperidinyl, 3-dimethylaminopyrrolidinyl, 3-methylaminopyrrolidinyl, 3-aminopirrolidinyl or methylmorpholinyl.

The term "alkenyl" comprises preferably branched and non branched alkenyls as for example vinyl, propen-1-yl, propen-2-yl, but-1-en-1-yl, but-1-en-2-yl, but-2-en-1-yl, but-2-en-2-yl, but-1-en-3-yl, 2-methylo-prop-2-en-1-yl, 2-methyl-prop-1-en-1-yl and their corresponding isomers.

The term "alkynyl" comprises preferably branched and non branched alkynyls as for example ethinyl, prop-1-in-1-yl, but-1-in-1-yl, but-2-in-1-yl, but-3-in-1-yl, and their corresponding isomers.

The term "aryl" is defined in each case as those which contain from 3 to 12 carbon atoms, preferably 6-12 carbon atoms as for example cyclopropenyl, phenyl, tropyl, indenyl, naphthyl, azulenyl, biphenyl, fluorenyl, anthracenyl etc, preferably phenyl.

The term "heteroaryl" is defined as a system of aromatic rings that comprises 3-16 rings preferably rings with 5 or 6 or 9 or 10 atoms that contain at least one heteroatom being as identical or different to the heteroatoms cited before being as for example Nitrogen (N), NH, $NR^{d3}$, O, S and may be monocyclic, bicyclic or tricyclic.

Furthermore, in this case it can be benzocondensated. Preferably the heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazoleyl, tia-4H-pyrazolyl etc., and benzoderivatives as for example benzofuranyl, benzothienyl, benzoxazolyl, benzimidazolyl, benzotriazolyl, indazolyl, indolyl, isoindolyl, etc. or pyridyl, pyridazinyl, primidinyl, pyrazinyl, triazinyl, etc., other benzoderivatives like for example quinolinyl, isoquinolinyl, etc., or azocinyl, indolizinyl, purinyl, etc., and also other benzoderivatives like cinnolinyl, phthalazinyl, quinazolinyl, quinoxalinyl, naphthpyridinylo, pteridinyl, carbazolyl, acrydinyl, fenazinyl, fenothiazinyl, fenoxazinyl, xantenyl, or oxepinyl, etc.

The term "$C_1$-$C_6$" is used related to the text as for example in the context of the definition "$C_1$-$C_6$ alkyl", or "$C_1$-$C_6$ alkoxide" as the alkyl groups that have a finite carbon atom number from 1 to 6, in other words, 1, 2, 3, 4, 5 or 6 carbon atoms. The term "$C_1$-$C_6$" is understood as any subinterval comprised from $C_1$-$C_6$, $C_2$-$C_6$, $C_3$-$C_4$, $C_1$-$C_2$, $C_1$-$C_3$, $C_1$-$C_4$, $C_1$-$C_5$ preferably $C_1$-$C_2$, $C_1$-$C_3$, $C_1$-$C_4$, $C_1$-$C_5$, $C_1$-$C_6$; more preferably $C_1$-$C_3$.

In the same way, the term used as "$C_2$-$C_6$" is used in that related to the text as for example in the context of the definitions "$C_2$-$C_6$ alkenyl", or "$C_2$-$C_6$ alkynyl" are understood like alkenyl or alkynyl groups with a finite number of carbon atoms from 2 to 6, in other words 2, 3, 4, 5 or 6 carbon atoms. It is understood that the term "$C_2$-$C_6$" implies any subinterval comprised from $C_2$-$C_6$, $C_3$-$C_5$, $C_3$-$C_4$, $C_2$-$C_3$, $C_2$-$C_4$, $C_2$-$C_5$; preferably $C_2$-$C_3$.

In the same way the term used as "$C_2$-$C_6$" is used in that related to the text for example in the context of the definitions "$C_3$-$C_{10}$ cycloalkyl", it is understood as alkenyl or alkynyl groups with a finite number of carbon atoms from 3 to 10, in other words, 3, 4, 5, 6, 7, 8, 9 or 10 carbon atoms, preferably 3, 4, 5 or 6 carbon atoms. It is understood that the term "$C_3$-$C_{10}$" implies any subinterval comprised from $C_3$-$C_{10}$, $C_4$-$C_9$, $C_5$-$C_8$, $C_6$-$C_7$, preferably $C_3$-$C_6$. In the same way, the term used as "$C_3$-$C_7$" is used in that related to the text for example in the context of the definitions "$C_3$-$C_7$-cycloalkyl", "$C_3$-$C_7$-heterocycloalkyl", it is understood as cycloalkyl groups with a finite number of carbon atoms from 3 to 6, in other words 3, 4, 5 or 6 carbon atoms. It is understood that the term "$C_3$-$C_6$" implies any subinterval comprised from $C_3$-$C_4$, $C_4$-$C_6$, $C_5$-$C_6$.

In the same way the term used as "$C_6$-$C_n$" is used in that related to the text for example "$C_6$-$C_n$-arilo", it is understood as aryl groups with a finite number of carbon atoms from 5 to 11, in other words, 5, 6, 7, 8, 9, 10 or 11 carbon atoms, preferably 5, 6 or 10 carbon atoms. It is understood that the term "$C_6$-$C_n$" implies any subinterval comprised from $C_5$-$C_{10}$, $C_6$-$C_9$, $C_7$-$C_8$; preferably $C_5$-$C_6$.

In the same way the term used as "$C_5$-$C_{10}$" is used in that related to the text in the context of the definitions "$C_5$-$C_{10}$-heteroaryl", it is understood as heteroaryl groups with a finite number of carbon atoms from 5 to 10 and also one or more heteroatoms present in the ring, in other words, 5, 6, 7, 8, 9 or 10 carbon atoms. Preferably, 5, 6 or 10 carbon atoms. It is understood that the term "$C_5$-$C_{10}$" implies any subinterval comprised from $C_6$-$C_9$, $C_7$-$C_8$, $C_7$-$C_8$; preferably $C_5$-$C_6$.

In the same way the term used as "$C_1$-$C_3$" is used in that related to the text in the context of the definitions "$C_1$-$C_3$ alkylene", it is understood as alkylene groups defined before with a finite number of carbon atoms from 1 to 3, in other words, 1, 2 or 3 carbon atoms. It is understood that the term "$C_1$-$C_3$" implies any subinterval comprised from $C_1$-$C_2$ or $C_2$-$C_3$.

In the same way the term used as "with at least one or more groups" for example in the definition of the substituents of compounds of the general formula (I) of the present invention, it is understood that they mean "one, two, three, four or five groups, particularly one, two, three or four groups, more particularly one, two or three groups, even more particularly one or two groups, and even more preferably one group".

The present invention comprises the isomers, constitutional isomers and stereoisomers of compounds of formula (I) and formula (II).

The term "isomers" is understood as chemical compounds with the same number and type of atoms as another chemical species. There are two types of isomers, constitutional isomers and stereoisomers.

Constitutional isomers are those in which the atoms and functional groups are joined together in different ways. These are functional isomers, structural isomers, tautomers or valence isomers.

The stereoisomers have the atoms joined together in the same way, therefore the two condensed formulas are identical. The isomers are different in the way the atoms are oriented in the space. There are two types of stereoisomers; conformational which can interconvert by rotation and configurational which cannot interconvert themselves.

In the configurational isomers are comprised the enantiomers and diastereomers. Enantiomers are related to the other isomer because they are as mirror-images. Enantiomers must contain a stereogenic centre, and each stereocentre is the mirror-image that corresponds to the other molecule. If one or more of these centres are different in configuration, both images are not mirror-images. Stereoisomers that are not enantiomers are called diastereomers or diastereoisomers.

Through the whole description and claims the word "comprises" and its variants do not pretend to exclude any other technical characteristics, additives, components, or pathways. For experts in the field, other objects, advantages and characteristics of the invention may be understood from both the description and the practice of the invention. The following examples and figures are given as illustration, and do not pretend to be limitative of the present invention.

Examples of the Invention

Synthesis of 1,2,4-thiadiazoles-5-imino substituted

[Göblyös, A., Vries, H., Brussee, J., IJzerman, A. "Synthesis and Biological evaluation of a new series of 2,3,5-substituted [1,2,4]-thiadiazoles as modulators of adenosine $A_1$ receptors and their molecular mechanism of action". *J Med Chem.* 2005 48, 1145-1151]

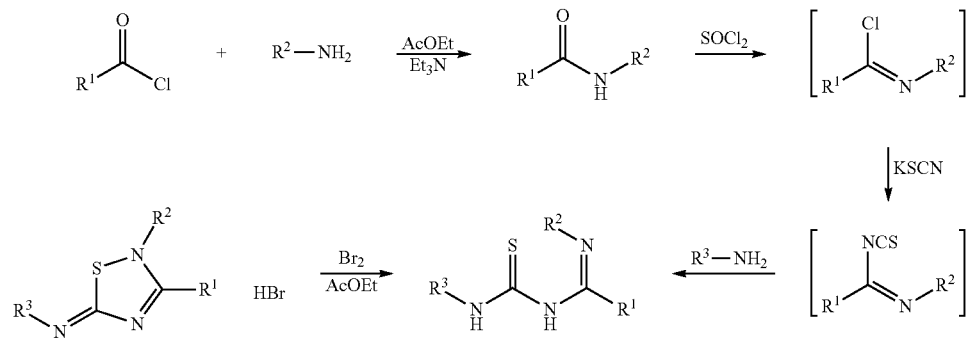

General Procedure for Imidoyl Chloride Synthesis Via Thionyl Chloride.

A mixture of the corresponding amide (1 equiv) with thionyl chloride (1.2 equiv) was heated at 135° C. for 4 h. Afterwards the resulting mixture was allowed to cool to room temperature, dichloromethane was added and the solvent and excess of thionyl chloride were evaporated under reduce pressure. The imidoyl chlorides obtained were used in the next step of the synthesis without further purification.

General Procedure for Imidoyl Chloride Synthesis Via Phosphorus Pentachloride.

[Claramunt, R. M., Santa-Maria, D., Pinilla, E., Torres, R., Elguero, J. "Structural Studies of Two Tinuvin® P analogs: 2-(2,4-Dimethylphenyl)-2H-benzotriazole and 2-phenyl-2H-benzotriazole". *Molecules* 2007, 12, 2201-2214]

An equimolar mixture of the corresponding amide with phosphorus pentachloride was heated in toluene under reflux for 4 h. Afterwards, the resulting mixture was allowed to cool to room temperature, the solids formed were filtered off and the solvent was evaporated under reduced pressure. The products obtained were used in the next step of the synthesis without further purification.

General Procedure for Imidoyl Chloride Synthesis Via Phosphorus Oxalyl Chloride

[Cunico, R., Pandey, R. "Palladium-Catalyzed Synthesis of α-Iminoamides from Imidoyl Chlorides and a Carbamoylsilane". *J. Org. Chem.* 2005, 70, 5344-5346]

Over a solution of the corresponding amide (1 equiv) in dichloromethane at 0° C., 2,6-lutidine (1.66 equiv) was added. Afterwards oxalyl chloride (1 equiv) was slowly added and the reaction mixture was left for 30 min. After evaporation of the solvent under reduced pressure, the product obtained was used in the next step of the synthesis without further purification.

General Procedure for Imidoylthioureas Synthesis:

Over a solution of the corresponding imidoyl chloride (1 equiv) in anhydrous acetone at −15° C., and under inert conditions, a solution of potassium thyocianate (1.1 equiv)

in acetone was slowly added. After the addition was completed, the mixture was allowed to reach 0° C., filtered through a plug of Celite and then the primary amine (1.1 equiv) was added at 0° C. The resulting reaction mixture was stirred at room temperature for 12-24 h. The solvent was then removed under reduced pressure and the remaining solid was purified with several methanol washes or flash column chromatography.

3-(N-Phenylbenzimidoyl)-1-(3-pyridylmethyl)thiourea (VP1.11)

N-phenylbenzimidoyl chloride (0.37 g, 1.72 mmol), potassium thyocianate (0.182 g, 1.89 mmol), 3-(aminomethyl)pyridine (0.190 ml, 1.89 mmol). The crude product was purified with several methanol washes to afford a yellow solid (0.366 g, 64%), mp 146-147° C. $^1$H NMR (CDCl$_3$) δ 12.48 (s, 1H), 8.68 (s, 1H), 8.55 (d, 1H, J=4.2 Hz), 8.15 (s, 1H) 7.84 (dd, 1H, J=1.7 Hz, 7.68 Hz), 7.68-6.94 (m, 9H), 6.64 (d, 2H, J=6.8 Hz), 5.0 (d, 2H, J=5.0 Hz). $^{13}$C NMR (CDCl$_3$) δ 181.2, 155.7, 149.0, 148.7, 146.2, 135.7, 132.9, 131.9, 130.7, 128.8, 128.1, 123.9, 123.6, 122.3, 46.7. HPLC: Purity >99% r.t.=3.65 min. MS (ESI+): 347 [M+H].

1-Ethoxycarbonylmethyl-3-(N-phenylbenzimidoyl)thiourea (VP1.13)

N-phenylbenzimidoyl chloride (0.355 g, 1.65 mmol), potassium thyocianate (0.176 g, 1.81 mmol). Ethyl aminoacetate hydrochloride (0.193 g, 1.81 mmol) was used after stirred in anhydrous acetone for 15 min at room temperature with sodium bicarbonate (0.456 g, 5.43 mmol). The crude product was purified with several methanol washes to afford pale orange solid (225 mg, 40%), mp 151-152° C. $^1$H NMR (CDCl$_3$) δ 12.46 (s, 1H), 8.08 (s, 1H), 7.34-6.93 (m, 8H), 6.70 (d, 2H, J=7.5 Hz), 4.50 (d, 2H, J=4.3 Hz), 4.23 (q, 2H, J=7.2 Hz), 1.26 (t, 3H, J=7.2 Hz). $^{13}$C NMR (CDCl$_3$) δ 180.7, 168.7, 155.2, 132.0, 130.6, 130.5, 129.1, 128.8, 128.8, 128.0, 124.0, 122.4, 61.6, 47.5, 14.1. HPLC: Purity >99% r.t.=4.97 min. MS (ESI+): 342 [M+H].

1-(2-Hydroxyethyl)-3-(N-phenylbenzimidoyl)thiourea (VP1.12)

N-phenylbenzimidoyl chloride (0.643 g, 2.98 mmol), potassium thyocianate (0.317 g, 3.26 mmol), 2-aminoethanol (0.196 ml, 3.26 mmol). The crude product was purified with several methanol washes to afford a pale yellow solid (481 mg, 54%) mp 144-145° C. $^1$H NMR (CDCl$_3$) δ 12.24 (s, 1H), 8.09 (s), 7.37-6.91 (m, 8H), 6.68 (d, 2H, J=7.5 Hz), 3.93 (s, 4H), 2.24 (bs, 1H). $^{13}$C NMR (CDCl$_3$) δ 181.1, 155.6, 146.5, 132.1, 130.7, 130.5, 129.4, 129.1, 128.8, 128.9, 128.3, 128.2, 123.9, 122.4, 61.6, 47.7. HPLC: Purity 97% r.t.=3.92 min. MS (ESI+): 300 [M+H].

1-Pentyl-3-(N-phenylbenzimidoyl)thiourea (VP1.19)

N-phenylbenzimidoyl chloride (1.68 g, 7.8 mmol), potassium thyocianate (0.835 g, 8.6 mmol), pentylamine (0.995 ml, 8.6 mmol). The crude product was purified with several methanol washes to afford a brown solid (785 mg, 31%) mp 157-158° C. $^1$H NMR (CDCl$_3$) δ 11.99 (s, 1H), 8.00 (s, 1H), 7.41-6.92 (m, 8H), 6.68 (d, 2H, J=7.5 Hz) 3.71 (td, J=7.1 Hz; 5.5 Hz; 2H), 1.71 (q, J=7.5 Hz; 2H), 1.47-1.28 (m, 4H), 0.90 (t, J=7.0 Hz; 3H). $^{13}$C NMR (CDCl$_3$) δ 179.8, 155.6, 146.6, 132.1, 130.5, 128.7, 128.7, 128.1, 123.7, 122.3, 45.9, 29.2, 28.0, 22.3, 13.9. HPLC: Purity >99% r.t.=5.91 min. MS (ESI+): 326 [M+H].

3-(N-Phenyl-4-methoxyphenylacetimidoyl)-1-(3-pyridylmethyl)-thiourea (VP1.35)

N-phenyl-(4-methoxypheny)acetimidoyl chloride (1.078 g, 4.4 mmol), potassium thyocianate (0.470 mg, 4.84 mmol), 3-(aminomethyl)pyridine (0.490 ml, 4.84 mmol). The crude product was purified with several methanol washes to afford a grey solid (761 mg, 46%) mp 175-176° C. $^1$H NMR (CDCl$_3$) δ 12.45 (s, 1H), 8.59 (s, 1H), 8.51 (s, 1H), 8.04 (s, 1H), 7.77-7.61 (m, 1H), 7.25-6.43 (m, 10H), 4.92 (d, J=5.4 Hz, 2H), 3.71 (s, 3H). $^{13}$C NMR (CDCl$_3$) δ 181.4, 161.1, 155.4, 149.0, 148.7, 135.8, 129.8, 128.8, 123.6, 122.4, 114.2, 55.3, 46.7. HPLC: Purity 96% r.t.=2.89 min. MS (ESI+): 377 [M+H].

1-(2-Hydroxyethyl)-3-(N-phenyl-4-methoxyphenylacetimidoyl)thiourea (VP1.36)

N-phenyl-(4-methoxyphenyl)acetimidoyl chloride (1.078 g, 4.4 mmol), potassium thyocianate (0.470 g, 4.84 mmol), 2-aminoethanol (0.290 ml, 4.84 mmol). The crude product was purified by flash chromatography (CH$_2$Cl$_2$:MeOH 80:1) to afford a white solid (767 mg, 53%) mp 117-119° C. $^1$H NMR (CDCl$_3$) δ 12.28 (s, 1H), 8.05 (s, 1H), 7.35-6.57 (m, 9H), 3.93 (m, 4H), 3.77 (s, 3H). $^{13}$C NMR (CDCl$_3$) δ 181.7, 161.5, 155.6, 147.1, 130.3, 129.2, 124.5, 124.1, 122.8, 114.5, 62.2, 55.7, 48.09. HPLC: Purity 97% r.t.=3.83 min. MS (ESI+): 330 [M+H].

1-Ethoxycarbonylmethyl-3-(N-phenyl-4-methoxyphenylacetimidoyl)thiourea (VP1.37)

N-phenyl-4-methoxyphenylacetimidoyl chloride (1.078 g, 4.4 mmol), potassium thyocianate (0.470 g, 4.84 mmol). Ethyl aminoacetate hydrochloride (0.675 g, 4.84 mmol) was used after stirred in anhydrous acetone for 15 min at room temperature with sodium bicarbonate (1.219 g, 14.52 mmol). The crude product was purified by flash chromatography (AcOEt/Hexane 1:1) to afford a white solid (457 mg, 28%) mp 120-121° C. $^1$H NMR (CDCl$_3$) δ 12.52 (s, 1H), 8.09 (s, 1H), 7.38-6.59 (m, 9H), 4.51 (d, J=4.8 Hz, 2H), 4.24 (q, J=7.1 Hz, 2H), 3.77 (s, 3H), 1.27 (t, J=7.2 Hz, 3H). $^{13}$C NMR (CDCl$_3$) δ 181.1, 168.8, 161.3, 155.2, 146.8, 130.1, 129.0, 124.2, 124.0, 122.7, 114.4, 61.8, 55.6, 47.7, 14.4. HPLC: Purity 96% r.t.=5.00 min. MS (ESI+): 372 [M+H].

1-Pentyl-3-(N-phenyl-4-methoxyphenylacetimidoyl)thiourea (VP1.38)

N-phenyl-4-methoxyphenylacetimidoyl chloride (1.163 g, 4.75 mmol), potassium thyocianate (0.510 mg, 5.2 mmol), pentylamine (0.370 ml, 5.2 mmol). The crude product was purified with several methanol washes to afford a brown solid (792 mg, 47%) mp 125-126° C. $^1$H NMR (CDCl$_3$) δ 11.98 (s, 1H), 7.99 (s, 1H), 7.27-6.55 (m, 9H), 3.69 (s, 3H), 3.62 (m, 2H), 1.71-1.57 (m, 2H), 1.29 (d, J=3.3 Hz, 4H), 0.81 (t, J=6.9 Hz, 3H). $^{13}$C NMR (CDCl$_3$) δ 180.4, 161.4, 155.8, 147.3, 130.3, 129.2, 124.6, 124.0, 122.8, 114.8, 114.5, 55.7, 46.2, 31.3, 29.6, 28.5, 22.7, 14.4. HPLC: Purity >99% r.t.=5.88 min. MS (ESI+): 356 [M+H].

3-(N-4-Methoxyphenylbenzimidoyl)-1-(3-pyridylmethyl)thiourea (VP1.57)

N-(4-methoxyphenyl)benzimidoyl chloride (1.08 g, 4.4 mmol), potassium thyocianate (0.500 g, 5.15 mmol), 3-(aminomethyl)pyridine (0.521 ml, 5.15 mmol). The crude product was purified with several methanol washes to afford a yellow solid (612 mg, 37%) mp 142-143° C. $^1$H NMR (CDCl$_3$) δ 12.53 (s, 1H), 8.59 (s, 1H), 8.48 (dd, J=4.8 Hz, 1.4 Hz, 1H), 8.05 (s, 1H), 7.73 (d, J=7.7 Hz, 1H), 7.37-7.09 (m, 6H), 6.58 (d, J=8.5 Hz, 2H), 6.47 (d, J=8.2 Hz, 2H), 4.92 (d, J=4.6 Hz, 2H), 3.64 (s, 3H). $^{13}$C NMR (CDCl$_3$) δ 181.6, 156.7, 155.9, 149.6, 149.4, 139.7, 136.1, 133.3, 132.6, 131.1, 129.3, 128.5, 124.0, 123.8, 114.5, 55.7, 47.2. HPLC: Purity 98.6% r.t.=2.75 min. MS (ESI+): 377 [M+H].

1-(2-Hydroxyethyl)-3-(N-4-methoxyphenylbenzimidoyl)thiourea (VP1.58)

N-(4-methoxyphenyl)benzimidoyl chloride (1.150 g, 4.68 mmol), potassium thyocianate (0.500 g, 5.15 mmol), 2-aminoethanol (0.310 ml, 5.15 mmol). The crude product was purified with several methanol washes to afford a white solid (508 mg, 33%) mp 141-142° C. $^1$H NMR (CDCl$_3$) δ 12.39 (s, 1H), 8.05 (s, 1H), 7.35 (m, 5H), 6.70 (m, 4H), 3.98 (s, 4H), 3.76 (s, 3H), 2.20 (s, 1H). $^{13}$C NMR (CDCl$_3$) δ 181.6, 155.7, 139.9, 130.92, 129.3, 128.5, 123.9, 114.5, 62.2, 55.8, 48.1, 181.2, 169.1, 156.7, 155.3, 139.7, 132.7, 130.9, 129.3, 128.4, 124.0, 114.4, 62.0, 55.8, 47.9. HPLC: Purity >99% r.t.=3.85 min. MS (ESI+): 330 [M+H].

1-Ethoxycarbonylmethyl-3-(N-4-methoxyphenyl-benzymidoyl)thiourea (VP1.59)

N-(4-methoxyphenyl)benzimidoyl chloride (1.08 g, 4.4 mmol), potassium thyocianate (0.500 g, 5.15 mmol). Ethyl aminoacetate hydrochloride (0.720 g, 5.15 mmol) was used after stirred in anhydrous acetone for 15 min at room temperature with sodium bicarbonate (1.30 g, 15.45 mmol). The crude product was purified with several methanol washes to afford a orange solid (489 mg, 30%) mp 146-147° C. $^1$H NMR (CDCl$_3$) δ 12.54 (s, 1H), 7.97 (s, 1H), 7.57-7.02 (m, 5H), 6.59 (s, 4H), 4.45 (s, 2H), 4.19 (q, J=7.1 Hz, 2H), 3.65 (s, 3H), 1.22 (t, J=7.1 Hz, 3H). $^{13}$C NMR (CDCl$_3$) δ 181.2, 169.1, 156.7, 155.3, 139.7, 132.7, 130.9, 129.3, 128.4, 124.0, 114.4, 62.0, 55.8, 47.9, 14.6. HPLC: Purity 97% r.t.=4.84 min. MS (ESI+): 372 [M+H].

1-Phenyl-3-(N-phenylbenzimidoyl)thiourea (VP1.20)

N-phenylbenzimidoyl chloride (1.68 g, 7.8 mmol), potassium thyocianate (0.835 g, 8.6 mmol), aniline (0.783 ml, 8.6 mmol). The crude product was purified with several methanol washes to afford a yellow solid (1.45 g, 54%) mp 143-144° C. (lit. 141-142° C.). $^1$H NMR (CDCl$_3$) δ 14.09 (s, 1H), 8.15 (s, 1H), 8.0-7.0 (m, 13H) 6.75 (d, J=7.5 Hz; 2H). $^{13}$C NMR (CDCl$_3$) δ 178.8, 155.8, 146.0, 138.2, 132.0, 130.7, 129.0, 128.9, 128.9, 128.2, 126.5, 124.1, 124.0, 122.4. HPLC: Purity 95% r.t.=5.26 min. MS (ESI+): 332 [M+H].

3-(N-4-Nitrophenylbenzimidoyl)-1-(3-pyridylmethyl)thiourea (VP2.1)

N-(4-nitrophenyl)benzimidoyl chloride (1.144 g, 4.12 mmol), potassium thyocianate (0.730 g, 4.53 mmol), 3-(aminomethyl)pyridine (0.460 ml, 4.53 mmol). The crude product was purified with several methanol washes to afford a yellow solid (1.256 g, 78%) mp 179-180° C. $^1$H NMR (CDCl$_3$) δ 11.95 (s, 1H), 8.71 (s, 1H), 8.59 (d, J=4.3 Hz, 1H), 8.24 (s, 1H), 8.02 (d, J=8.9 Hz, 1H), 7.95 (d, J=8.1 Hz, 1H), 7.51-7.17 (m, 7H), 6.77 (d, J=8.8 Hz, 2H), 5.04 (d, J=5.5 Hz, 2H). $^{13}$C NMR (CDCl$_3$) δ 177.4, 167.4, 160.0, 131.5, 129.3, 128.0, 124.8, 123.0, 29.7. HPLC: Purity 95.1% r.t.=3.37 min. MS (ESI+): 392 [M+H].

1-Ethoxycarbonylmethyl-3-(N-4-nitrophenylbenzimidoyl)thiourea (VP2.5)

N-(4-nitrophenyl)benzimidoyl chloride (1.144 g, 4.12 mmol), potassium thyocianate (0.730 g, 4.53 mmol). Ethyl aminoacetate hydrochloride (0.630 g, 4.53 mmol) was used after stirred in anhydrous acetone for 15 min at room temperature with sodium bicarbonate (1.14 g, 13.6 mmol). The crude product was purified with several methanol washes to afford a pale yellow solid (636 mg, 63%) mp 189-190° C. $^1$H NMR (CDCl$_3$) δ 12.00 (s, 1H), 8.27 (s, 1H), 8.04 (d, J=8.9 Hz, 2H), 7.57-7.12 (m, 5H), 6.84 (d, J=8.9 Hz, 2H), 4.50 (d, J=4.7 Hz, 2H), 4.25 (q, J=7.1 Hz, 2H), 1.28 (t, J=7.1 Hz, 3H). $^{13}$C NMR (CDCl$_3$) δ 180.2, 168.5, 156.1, 144.0, 131.4, 131.0, 129.2, 128.0, 124.7, 123.0, 61.8, 47.6, 14.1. HPLC: Purity >99% r.t.=5.13 min. MS (ESI+): 387 [M+H].

3-(N-Phenyl-4-trifluoromethylphenylacetimidoyl)-1-(3-pyridylmethyl)thiourea (VP2.42)

N-phenyl-4-trifluoromethylphenylacetimidoyl chloride (0.580 g, 2.05 mmol), potassium thyocianate (0.220 g, 2.26 mmol), 3-(aminomethyl)pyridine (0.230 ml, 2.26 mmol). The crude product was purified with several methanol washes to afford a white solid (339 mg, 40%) mp 165-166° C. $^1$H NMR (CDCl$_3$) δ 12.32 (s, 1H), 8.68 (s, 1H), 8.54 (d, J=4.9 Hz, 1H), 8.29 (s, 1H), 7.81 (d, J=7.9 Hz, 1H), 7.60-6.81 (m, 8H), 6.63 (s, 2H), 4.98 (d, J=5.1 Hz, 2H). $^{13}$C NMR (CDCl$_3$) δ 181.3, 149.0, 148.8, 136.3, 133.2, 129.3, 128.9, 126.1, 124.7, 123.9, 122.4, 47.0. HPLC: Purity >99% r.t.=3.83 min. MS (ESI+): 415 [M+H].

3-(N-1-Naphthylbenzimidoyl)-1-(3-pyridylmethyl)thiourea (VP2.8)

N-naphthyl-benzimidoyl chloride (1.940 g, 4.9 mmol), potassium thyocianate (0.523 g, 5.39 mmol), 3-(aminomethyl)pyridine (0.540 ml, 5.39 mmol). The crude product was purified with several methanol washes to afford a white solid (1.125 mg, 58%) mp 153-154° C. $^1$H NMR (CDCl$_3$) δ 12.74 (s, 1H), 8.74 (s, 1H), 8.59 (d, J=4.8 Hz, 1H), 8.38 (bs, 1H), 8.00 (d, J=7.5 Hz, 1H), 7.94-7.76 (m, 1H), 7.55 (d, J=8.0 Hz, 1H), 7.43-6.96 (m, 9H), 6.50 (d, J=7.5 Hz, 2H), 5.09 (d, J=4.8 Hz, 2H). $^{13}$C NMR (CDCl$_3$) δ 181.8, 156.6, 149.6, 143.2, 132.3, 131.5, 129.3, 127.9, 124.8, 122.9, 117.9, 47.3. HPLC: Purity 97% r.t.=3.94 min. MS (ESI+): 397 [M+H].

1-(2-Hydroxyethyl)-3-(N-1-naphthylbenzimidoyl)thiourea (VP2.9)

N-naphthyl-benzimidoyl chloride (1.940 g, 4.9 mmol), potassium thyocianate (0.523 g, 5.39 mmol), 2-aminoethanol (0.325 ml, 5.39 mmol). The crude product was purified with several methanol washes to afford a white solid (410 mg, 24%) mp 131-132° C. $^1$H NMR (CDCl$_3$) δ 12.43 (s, 1H), 8.25 (s, 1H), 8.14 (d, J=7.2 Hz, 1H), 7.82 (d, J=6.5 Hz, 1H), 7.65-7.40 (m, 1H), 7.40-6.86 (m, 7H), 6.45 (d, J=6.8 Hz, 2H), 3.94 (s, 4H), 2.16 (s, 1H). $^{13}$C NMR (CDCl$_3$) δ 181.3, 155.9, 143.1, 133.9, 132.0, 130.6, 128.7, 128.1, 128.1, 127.5, 126.3, 126.1, 125.5, 124.0, 123.2, 117.2, 61.5, 47.7. HPLC: Purity 96% r.t.=4.82 min. MS (ESI+): 350 [M+H].

3-(N-Phenyl-1-naphthylacetimidoyl)-1-(3-pyridylmethyl)thiourea (VP2.27)

N-phenyl-1-naphthylacetimidoyl chloride (2.178 g, 5.5 mmol), potassium thyocianate (0.588 g, 6.06 mmol), 3-(Aminomethyl)pyridine (0.613 ml, 6.06 mmol). The crude product was purified with several methanol washes to afford a white solid (1.285 mg, 59%) mp 162-163° C. $^1$H NMR (CDCl$_3$) δ 12.65 (s, 1H), 8.76 (s, 1H), 8.60 (d, J=3.6 Hz, 1H), 8.14 (bs, 1H), 8.00 (d, J=8.1 Hz, 1H), 7.95-7.64 (m, 3H), 7.70-7.11 (m, 6H), 7.06-6.40 (m, 4H), 5.07 (s, 2H). $^{13}$C NMR (CDCl$_3$) δ 181.1, 155.8, 149.3, 149.0, 145.9, 135.9, 133.2, 132.9, 130.7, 130.0, 128.5, 128.4, 127.6, 127.3, 126.9, 126.7, 125.2, 124.8, 124.5, 124.2, 123.6, 121.7, 120.0, 46.8. HPLC: Purity 98% r.t.=3.90 min. MS (ESI+): 397 [M+H].

1-(2-Hydroxyethyl)-3-(N-phenyl-1-naphthylacetimidoyl)thiourea (VP2.28)

N-phenyl-1-naphthylacetimidoyl chloride (2.158 g, 5.45 mmol), potassium thyocianate (0.583 g, 6.00 mmol), 2-aminoethanol (0.362 ml, 6.00 mmol). The crude product was purified with several methanol washes to afford a white solid (932 mg, 49%) mp 155-156° C. $^1$H NMR (CDCl$_3$) δ 12.34 (s, 1H), 8.25 (s, 1H), 8.02-7.63 (m, 2H), 7.8-7.24 (m, 2H), 7.27-6.44 (m, 8H), 3.95 (s, 4H), 2.32 (s, 1H). $^{13}$C NMR (CDCl$_3$) δ 181.0, 133.1, 130.6, 130.0, 128.5, 127.5, 126.9, 124.7, 124.1, 121.8, 61.3, 47.6. HPLC: Purity 96% r.t.=4.71 min. MS (ESI+): 350 [M+H].

3-(N-Phenylacetimidoyl)-1-(3-pyridylmethyl)thiourea (VP2.58)

N-phenyl-acetimidoyl chloride (0.330 g, 2.16 mmol), potassium thyocianate (0.231 g, 2.38 mmol), 3-(aminomethyl)pyridine (0.240 ml, 2.38 mmol). The crude product was purified by flash chromatography (AcOEt/Hexane 1:1) to afford a white solid (196 mg, 32%) mp 143-144° C. $^1$H NMR (CDCl$_3$) δ 12.39 (s, 1H), 8.71 (s, 1H), 8.61 (s, 1H) 8.56 (d, J=4.3 Hz, 1H), 7.79-7.55 (m, 1H), 7.36-7.14 (m, 2H), 7.05 (m, 2H), 6.85-6.46 (m, 2H), 5.10-4.64 (m, 2H), 1.88 (s, 3H). $^{13}$C NMR (CDCl$_3$) δ 181.1, 155.6, 149.0, 148.8, 146.6, 135.4, 132.8, 128.9, 124.2, 123.5, 121.2, 119.8, 46.4, 18.1. HPLC: Purity 95% r.t.=2.96 min. MS (ESI+): 285 [M+H].

1-(4-Morpholinethyl)-3-(N-phenylbenzimidoyl)thiourea (VP3.13)

N-phenyl-benzimidoyl chloride (1.900 g, 8.84 mmol), potassium thyocianate (1.267 g, 9.73 mmol), 2-(4-morpholinyl) ethanamine (1.267 ml, 9.73 mmol). The crude product was purified with several methanol washes to afford a pale yellow solid (2.28 g, 70%) mp 167-168° C. $^1$H NMR (CDCl$_3$) δ 12.09 (s, 1H); 7.97 (s, 1H), 7.30-6.88 (m, 8H), 6.62 (d, 2H, J=7.5 Hz), 3.75 (m, 2H), 3.41 (m, 4H), 2.56 (m, 2H), 2.42 (m, 4H). $^{13}$C NMR (CDCl$_3$) δ 179.7, 154.9, 132.0, 130.7, 130.4, 129.0, 128.9, 128.7, 128.0, 124.0, 122.4, 66.7, 55.9, 53.1, 42.7. HPLC: Purity >99% r.t.=2.85 min. MS (ESI+): 370 [M+H].

General Procedure for Hydrobromide Iminothiadiazole Synthesis.

Over a mixture of the corresponding imidoylthiourea (1 equiv) in CH$_2$Cl$_2$/AcOEt (1:2) at 0° C., a solution of Br$_2$ in AcOEt (0.5 M, 2 equiv) was added dropwise. Upon completion of the addition, the resulting mixture was left stirring at 4° C. until starting material clearance (1-12 h). Then, the precipitate formed was isolated, washed with a mixture of pentane:ethyl acetate (3:1) and purified by recrystallization from MeOH/H$_2$O.

2,3-Diphenyl-5-(3-pyridinylmethylimino)-2,5-dihydro-1,2,4-thiadiazole dihydrobromide (VP1.14)

Imidoylthiourea VP1.11 (0.608 g, 1.75 mmol), bromine (0.180 ml, 3.5 mmol). Reaction time: 1 h. White solid (566 mg, 64%) mp 255-256° C. $^1$H NMR (DMSO) δ 10.39 (t, J=6.0 Hz; 1H), 8.99 (s, 1H), 8.83 (d, J=4.5 Hz; 1H), 8.51 (d, J=8.0 Hz; 1H), 7.98 (dd, J=7.9, 5.6 Hz, 1H), 7.62-7.26 (m, 10H), 5.13 (d, J=5.9 Hz; 2H). $^{13}$C NMR (DMSO) δ 176.7, 165.3, 144.1, 143.7, 136.6, 135.0, 133.4, 131.6, 130.9, 129.4, 128.2, 127.2, 127.1, 45.6. $^{15}$N NMR (DMSO) δ 250, 197, 145, 131. MS (ESI+): 345 [M−HBr$_2$]. Anal. (C$_{20}$H$_{18}$Br$_2$N$_4$S) C, H, Br, N, S. Calculated: C, 47.45%; H, 3.58%; N, 11.07%; S, 6.33%; Br, 31.57%. Found: C, 47.67%; H, 3.63%; N, 11.15%; S, 6.73%; Br, 31.86%.

5-Ethoxycarbonylmethylimino-2,3-diphenyl-2,5-dihydro-1,2,4-thiadiazole hydrobromide (VP1.16)

Imidoylthiourea VP1.12 (0.219 g, 0.64 mmol), bromine (0.065 ml, 1.26 mmol). Reaction time: 1 h. White solid (172 mg, 64%) mp 232-233° C. $^1$H NMR (DMSO) δ 10.05 (s, 1H), 7.68-7.29 (m, 10H), 4.60 (s, 2H), 4.19 (q, J=7.1 Hz; 2H), 1.22 (t, J=7.1 Hz; 3H). $^{13}$C NMR (DMSO) δ 176.8, 169.3, 165.3, 135.0, 134.4, 133.4, 131.8, 131.5, 131.2, 130.9, 130.9, 129.8, 129.4, 128.3, 127.1, 61.9, 46.6, 14.8. $^{15}$N NMR (DMSO) δ 260, 200, 130. MS (ESI+): 340 [M−Br]. Anal. (C$_{18}$H$_{18}$BrN$_3$O$_2$S) C, H, Br, N, S. Calculated: C, 51.43%; H, 4.32%; N, 10.00%; S, 7.63%; Br, 19.01%. Found: C, 51.37%; H, 4.40%; N, 10.17%; S, 7.68%; Br, 18.83%.

5-(2-Hydroxyethylimino)-2,3-diphenyl-2,5-dihydro-1,2,4-thiadiazole hydrobromide (VP1.15)

Imidoylthiourea VP1.13 (0.500 g, 1.65 mmol), bromine (0.167 ml, 3.25 mmol). Reaction time: 4 h. White solid (187 mg, 30%) mp 235-236° C. $^1$H NMR (DMSO) δ 10.00 (bs, 1H), 7.72-7.29 (m, 10H), 4.31 (bs, 1H), 3.80 (q, J=6.1 Hz; 2H), 3.69 (t, J=5.2 Hz; 2H). $^{13}$C NMR (DMSO) δ 175.7, 165.3, 134.4, 132.6, 130.8, 130.2, 128.6, 127.6, 126.6, 58.8, 47.4. MS (ESI+): 298 [M−Br]. Anal. (C$_{16}$H$_{16}$BrN$_3$OS) C, H, Br, N, S. Calculated: C, 50.80%; H, 4.26%; N, 11.11%; S, 8.48%; Br, 21.12%. Found: C, 50.72%; H, 4.15%; N, 11.25%; S, 8.65%; Br, 21.33%.

5-Pentylimino-2,3-diphenyl-2,5-dihydro-1,2,4-thiadiazole hydrobromide (VP1.22)

Imidoylthiourea VP1.19 (0.20 g, 0.62 mmol), bromine (0.063 ml, 1.22 mmol). Reaction time: 12 h. In this case no precipitate was formed. Solvent was evaporated under reduced pressure and the crude was washed with a mixture pentane:ethyl acetate (3:1). The crude was purified by MeOH/H$_2$O recrystallization to afford a pale brown solid (104 mg, 42%) mp 241-242° C. $^1$H NMR (DMSO) δ 10.05

(s, 1H), 7.75-7.19 (m, 10H), 3.73 (m; 2H), 1.78-1.61 (m, 2H), 1.51-1.22 (m, 4H), 0.91 (t, J=7.0 Hz; 3H). $^{13}$C NMR (DMSO) δ 175.6, 165.6, 134.8, 132.9, 131.1, 130.6, 130.6, 129.0, 128.0, 127.0, 45.2, 28.7, 28.4, 22.0, 14.2. MS (ESI+): 324 [M-Br]. Anal. ($C_{19}H_{22}BrN_3S$) C, H, Br, N, S. Calculated: C, 56.43%; H, 5.48%; N, 10.39%; S, 7.93%; Br, 19.76%. Found: C, 56.18%; H, 5.59%; N, 10.38%; S, 7.76%; Br, 19.98%.

5-(2-Hydroxyethylimino)-3-(4-methoxyphenyl)-2-phenyl-2,5-dihydro-1,2,4-thiadiazole hydrobromide (VP1.40)

Imidoylthiourea VP1.36 (0.600 g, 1.82 mmol), bromine (0.187 ml, 3.65 mmol). Reaction time: 4 h. White solid (341 mg, 46%) mp 193-194° C. $^1$H NMR (DMSO) δ 9.94 (t, J=4.9 Hz, 1H), 7.82-7.18 (m, 7H), 6.96 (d, J=9.0 Hz, 2H), 3.92-3.53 (m, 7H), 3.34 (bs, 1H). $^{13}$C NMR (DMSO) δ 175.0, 164.6, 162.6, 134.8, 132.5, 130.7, 130.3, 127.6, 118.4, 114.2, 58.8, 55.6, 47.3. MS (ESI+): 329 [M-Br]. Anal. ($C_{17}H_{18}BrN_3O_2S$) C, H, Br, N, S. Calculated: C, 50.01%; H, 4.44%; N, 10.29%; S, 7.85%; Br, 19.57%. Found: C, 49.87%; H, 4.70%; N, 10.20%; S, 7.59%; Br, 19.29%.

3-(4-Methoxyphenyl)-2-phenyl-5-(3-pyridylmethylimino)-2,5-dihydro-1,2,4-thiadiazole dihydrobromide (VP1.43)

Imidoylthiourea VP1.35 (0.606 g, 1.6 mmol), bromine (0.166 ml, 3.22 mmol). Reaction time: 3 h. White solid (483 mg, 56%) mp 204-205° C. $^1$H NMR (DMSO) δ 10.39 (s, 1H), 9.06 (d, J=1.7 Hz, 1H), 8.98-8.82 (m, 1H), 8.62 (dt, J=8.1 Hz, 1.5 Hz, 1H), 8.07 (dd, J=7.9 Hz, 5.8 Hz, 1H), 7.68-7.37 (m, 7H), 7.09-6.80 (m, 2H), 5.17 (d, J=5.8 Hz, 2H), 3.77 (s, 3H). $^{13}$C NMR (DMSO) δ 175.4, 163.9, 162.7, 143.8, 142.7, 136.3, 134.7, 132.6, 130.8, 130.4, 127.5, 126.6, 118.3, 114.2, 55.6, 44.7. MS (ESI+): 375[M–HBr$_2$]. Anal. ($C_{21}H_{20}Br_2N_4OS$) C, H, Br, N, S. Calculated: C, 47.03%; H, 3.76%; N, 10.45%; S, 5.98%; Br, 29.80%. Found: C, 46.87%; H, 3.90%; N, 10.60%; S, 5.87%; Br, 29.49%.

3-(4-Methoxyphenyl)-5-pentylimino-2-phenyl-2,5-dihydro-1,2,4-thiadiazole hydrobromide (VP1.44)

Imidoylthiourea VP1.38 (0.637 g, 1.79 mmol), bromine (0.184 ml, 3.59 mmol). Reaction time: 12 h. Pale brown solid (327 mg, 42%) mp 176-177° C. $^1$H NMR (DMSO) δ 10.01 (s, 1H), 7.72-7.45 (m, 7H), 6.95 (d, J=9.0 Hz, 2H), 3.76 (s, 3H), 3.71 (m, 2H), 1.67 (m, 2H), 1.49-1.27 (m, 4H), 0.89 (t, J=7.1 Hz, 3H). $^{13}$C NMR (DMSO) δ 174.5, 164.5, 162.6, 134.9, 132.5, 130.7, 130.3, 127.6, 118.5, 114.2, 55.6, 44.6, 28.3, 28.0, 21.6, 13.8. $^{15}$N NMR (DMSO) δ 245, 206, 133. MS (ESI+): 354 [M-Br]. Anal. ($C_{20}H_{25}BrN_3OS$) C, H, Br, N, S. Calculated: C, 55.30%; H, 5.57%; N, 9.67%; S, 7.38%; Br, 18.39%. Found: C, 55.08%; H, 5.68%; N, 9.72%; S, 7.22%; Br, 18.08%.

5-Ethoxycarbonylmethylimino-3-(4-methoxyphenyl)-2-phenyl-2,5-dihydro-1,2,4-thiadiazole hydrobromide (VP1.65)

Imidoylthiourea VP1.37 (0.400 g, 1.08 mmol), bromine (0.110 ml, 2.16 mmol). Reaction time: 2 h. White solid (150 mg, 31%) mp 171-172° C. $^1$H NMR (DMSO) δ 9.89 (t, J=5.6 Hz, 1H), 7.71-7.56 (m, 5H), 7.45 (d, J=9.0 Hz, 2H), 6.96 (d, J=9.0 Hz, 2H), 4.58 (s, 2H), 4.20 (q, J=7.1 Hz, 2H), 3.77 (s, 3H), 1.24 (t, J=7.1 Hz, 3H). $^{13}$C NMR (DMSO) δ 173.25, 168.8, 164.9, 163.4, 135.3, 133.3, 131.6, 131.1, 128.3, 119.0, 115.0, 61.9, 56.4, 46.5, 14.8. MS (ESI+): 370 [M-Br]. Anal. ($C_{19}H_{20}BrN_3O_3S$) C, H, Br, N, S. Calculated: C, 50.67%; H, 4.48%; N, 9.33%; S, 7.12%; Br, 17.74%. Found: C, 50.55%; H, 4.61%; N, 9.32%; S, 7.10%; Br, 17.67%.

2-(4-Methoxyphenyl)-3-phenyl-5-(3-pyridinylmethylimino)-2,5-dihydro-1,2,4-thiadiazole dihydrobromide (VP1.60)

Imidoylthiourea VP1.57 (0.400 g, 1.06 mmol), bromine (0.109 ml, 2.12 mmol). Reaction time: 3 h. White solid (62 mg, 13%) mp 192-193° C. $^1$H NMR (DMSO) δ 10.42 (t, J=5.9 Hz, 1H), 9.08 (s, 1H), 8.92 (d, J=5.3 Hz, 1H), 8.68 (d, J=8.2 Hz, 1H), 8.13 (dd, J=7.9 Hz, 5.8 Hz, 1H), 7.76-7.24 (m, 7H), 7.06 (d, J=8.9 Hz, 2H), 5.17 (d, J=5.9 Hz, 2H), 3.79 (s, 3H). $^{13}$C NMR (DMSO) δ 176.6, 165.4, 161.3, 144.6, 143.1, 136.4, 133.3, 130.9, 129.7, 129.4, 127.3, 127.2, 126.8, 116.0, 56.4, 45.5. MS (ESI+): 375[M–HBr$_2$]. Anal. ($C_{21}H_{20}Br_2N_4OS$) C, H, Br, N, S. Calculated: C, 47.03%; H, 3.76%; N, 10.45%; S, 5.98%; Br, 29.80%. Found: C, 46.75%; H, 4.08%; N, 10.2%; S, 5.45%; Br, 29.45%.

5-(2-Hydroxyethylimino)-2-(4-methoxyphenyl)-3-phenyl-2,5-dihydro-1,2,4-thiadiazole hydrobromide (VP1.61)

Imidoylthiourea VP1.58 (0.400 g, 1.22 mmol), bromine (0.120 ml, 2.44 mmol). Reaction time: 2 h. White solid (49 mg, 10%) mp 195-196° C. $^1$H NMR (DMSO) δ 9.89 (t, J=5.3 Hz, 1H), 7.58-7.49 (m, 5H), 7.43 (d, J=9.7 Hz, 2H), 7.05 (d, J=8.9 Hz, 2H), 3.78 (s, 3H), 3.76 (m, 2H), 3.68 (m, 2H), 3.33 (bs, 1H). $^{13}$C NMR (DMSO) δ 175.9, 165.7, 160.9, 132.9, 130.6, 129.5, 129.0, 127.1, 127.0, 115.6, 59.2, 56.0, 47.7. MS (ESI+): 329 [M-Br]. Anal. ($C_{19}H_{20}BrN_3O_3S$) C, H, Br, N, S. Calculated: C, 50.67%; H, 4.48%; N, 9.33%; S, 7.12%; Br, 17.74%. Found: C, 50.40%; H, 4.61%; N, 9.45%; S, 6.98%; Br, 17.65%.

5-Ethoxycarbonylmethylimino-2-(4-methoxyphenyl)-3-phenyl-2,5-dihydro-1,2,4-thiadiazole hydrobromide (VP1.62)

Imidoylthiourea VP1.59 (0.400 g, 1.07 mmol), bromine (0.110 ml, 2.15 mmol). Reaction time: 2 h. White solid (48 mg, 10%) mp 189-190° C. $^1$H NMR (DMSO) δ 9.90 (t, J=5.5 Hz, 1H), 7.79-7.24 (m, 7H), 7.06 (d, J=8.9 Hz, 2H), 4.58 (d, J=5.7 Hz, 2H), 4.20 (q, J=7.1 Hz, 2H), 3.79 (s, 3H), 1.23 (t, J=7.1 Hz, 3H). $^{13}$C NMR (DMSO): δ 176.0, 168.1, 165.0, 160.6, 132.6, 130.2, 129.1, 128.6, 126.5, 115.2, 61.2, 55.6, 45.8, 14.0. MS (ESI+): 370 [M-Br]. Anal. ($C_{19}H_{20}BrN_3O_3S$) C, H, Br, N, S. Calculated: C, 50.67%; H, 4.48%; N, 9.33%; S, 7.12%; Br, 17.74%. Found: C, 50.40%; H, 4.61%; N, 9.45%; S, 6.98%; Br, 17.65%.

2,3-Diphenyl-5-phenylimino-2,5-dihydro-1,2,4-thiadiazole hydrobromide (VP1.23)

Imidoylthiourea VP1.20 (0.20 g, 0.60 mmol), bromine (0.061 ml, 1.19 mmol). Reaction time: 12 h. Yellow solid (132 mg, 54%) mp 230-231° C. (lit.[21] 227-228° C.). $^1$H NMR (DMSO) δ 12.41 (s, 1H), 8.50-6.51 (m, 15H). $^{13}$C NMR (DMSO) δ 178.6, 171.1, 142.8, 139.7, 138.5, 136.7, 136.1, 135.9, 135.4, 134.4, 133.8, 132.1, 131.6, 125.7, 100.0. MS (ESI+): 330 [M-Br]. Anal. ($C_{20}H_{16}BrN_3S$) C, H, Br, N, S. Calculated: C, 58.54%; H, 3.93%; N, 10.24%; S, 7.81%; Br, 19.47%. Found: C, 58.55%; H, 3.79%; N, 10.27%; S, 7.59%; Br, 19.56%.

2-(4-Nitrophenyl)-3-phenyl-5-(3-pyridinylmethylimino)-2,5-dihydro-1,2,4-thiadiazole dihydrobromide (VP2.12)

Imidoylthiourea VP2.1 (0.700 g, 1.79 mmol) bromine (0.184 ml, 3.58 mmol). Reaction time: 3 h. Yellow solid (128 mg, 13%) mp 242-243° C. $^1$H NMR (DMSO) δ 10.51 (s, 1H), 9.03 (s, 1H), 8.87 (d, J=5.4 Hz, 1H), 8.56 (d, J=8.0 Hz, 1H), 8.38 (d, J=9.0 Hz, 2H), 8.02 (dd, J=8.0 Hz, 5.5, 1H), 7.83 (d, J=9.0 Hz, 2H), 7.64-7.38 (m, 5H), 5.19 (d, J=5.0 Hz, 2H). $^{13}$C NMR (DMSO) δ 176.7, 165.2, 148.4, 143.7, 140.2, 136.3, 133.8, 130.8, 129.4, 129.2, 126.8, 126.6, 125.8, 45.4. MS (ESI+): 390[M–HBr$_2$]. Anal. (C$_{20}$H$_{17}$Br$_2$N$_5$O$_2$S) C, H, Br, N, S. Calculated: C, 43.58%; H, 3.11%; N, 12.70%; S, 5.82%; Br, 28.99%. Found: C, 43.29%; H, 3.15%; N, 12.57%; S, 5.71%; Br, 28.63%.

5-Ethoxycarbonylmethylimino-2-(4-nitrophenyl)-3-phenyl-2,5-dihydro-1,2,4-thiadiazole hydrobromide (VP2.14)

Imidoylthiourea VP2.5 (0.600 g, 1.55 mmol), bromine (0.160 ml, 3.1 mmol). Reaction time: 4 h. Pale yellow solid (461 mg, 64%) mp 225-226° C. $^1$H NMR (DMSO) δ 10.00 (t, J=5.7 Hz, 1H), 8.37 (d, J=8.9 Hz, 2H), 7.87 (d, J=8.9 Hz, 2H), 7.67-7.20 (m, 5H), 4.62 (d, J=5.6 Hz, 2H), 4.20 (q, J=7.1 Hz, 2H), 1.23 (t, J=7.1 Hz, 3H). $^{13}$C NMR (DMSO) δ 176.8, 168.3, 165.5, 148.4, 140.1, 133.3, 130.8, 129.5, 129.2, 126.6, 125.8, 61.6, 46.4, 14.4. MS (ESI+): 385 [M-Br]. Anal. (C$_{18}$H$_{17}$BrN$_4$O$_4$S) C, H, Br, N, S. Calculated: C, 46.46%; H, 3.68%; N, 12.04%; S, 6.89%; Br, 17.17%. Found: C, 46.39%; H, 3.63%; N, 12.11%; S, 6.71%; Br, 17.42%.

3-(4-Trifluoromethylphenyl)-2-phenyl-5-(3-pyridylmethylimino)-2,5-dihydro-1,2,4-thiadiazole dihydrobromide (VP2.45)

Imidoylthiourea VP2.42 (0.300 g, 0.72 mmol), bromine (0.074 ml, 1.45 mmol). Reaction time: 4 h. White solid (60 mg, 33%) mp 177-178° C. $^1$H NMR (DMSO) δ 10.84 (t, J=6.0 Hz, 1H), 9.01 (s, 1H), 8.88 (d, J=5.3 Hz, 1H), 8.59 (d, J=8.0 Hz, 1H), 8.05 (dd, J=7.9, 5.6 Hz, 1H), 7.82 (d, J=8.5 Hz, 2H), 7.80-7.62 (m, 2H), 7.64-7.41 (m, 5H), 5.15 (d, J=6.0 Hz, 2H). $^{13}$C NMR (DMSO) δ 176.7, 162.9, 145.5, 141.4, 137.0, 133.9, 131.1, 130.9, 130.2, 127.4, 125.6, 125.5, 44.6. MS (ESI+): 413[M–HBr$_2$]. Anal. (C$_{21}$H$_{17}$F$_3$Br$_2$N$_4$S) C, H, Br, N, S. Calculated: C, 43.77%; H, 3.32%; N, 9.72%; S, 5.56%; Br, 27.73%. Found: C, 43.51%; H, 3.58%; N, 9.60%; S, 5.39%; Br, 27.38%.

2-(1-Naphthyl)-3-phenyl-5-(3-pyridylmethylimino)-2,5-dihydro-1,2,4-thiadiazole dihydrobromide (VP2.15)

Imidoylthiourea VP2.8 (0.600 g, 1.51 mmol), bromine (0.156 ml, 3.03 mmol). Reaction time: 24 h. White solid (674 mg, 80%) mp 205-206° C. $^1$H NMR (DMSO) δ 10.52 (s, 1H), 9.09 (s, 1H), 8.90 (d, J=5.2 Hz, 1H), 8.65 (d, J=8.0 Hz, 1H), 8.28-7.24 (m, 13H), 5.24 (d, J=5.2 Hz, 2H). $^{13}$C NMR (DMSO) δ 176.7, 165.4, 143.8, 142.9, 142.8, 136.2, 133.7, 132.9, 131.7, 130.3, 129.6, 128.9, 128.8, 128.7, 127.8, 127.6, 126.6, 126.5, 125.8, 121.7, 45.0. MS (ESI+): 395[M–HBr$_2$]. Anal. (C$_{24}$H$_{20}$Br$_2$N$_4$S) C, H, Br, N, S. Calculated: C, 51.82%; H, 3.62%; N, 10.07%; S, 5.76%; Br, 28.73%. Found: C, 51.80%; H, 3.73%; N, 9.97%; S, 5.54%; Br, 28.45%.

5-(2-Hydroxyethylimino)-2-(1-naphthyl)-3-phenyl-2,5-dihydro-1,2,4-thiadiazole hydrobromide (VP2.16)

Imidoylthiourea VP2.9 (0.418 g, 1.97 mmol), bromine (0.123 ml, 2.39 mmol). Reaction time: 24 h. White solid (266 mg, 52%) mp 154-155° C. $^1$H NMR (DMSO) δ 10.19 (t, J=5.7 Hz, 0.5H, E-NH), 10.10 (t, J=5.6 Hz, 0.5H, Z—NH), 8.24-8.14 (m, 1H), 8.16 8.06 (m, 2H), 8.00-7.92 (m, 1H), 7.92-7.83 (m, 2H), 7.71-7.52 (m, 2H), 7.56-7.38 (m, 2H), 7.38-7.13 (m, 2H), 4.36 (t, J=5.3 Hz, 1H, E-CH$_2$—N), 4.07 (dd, J=7.6, 5.8 Hz, 1H, E-CH$_2$), 3.87 (dd, J=8.2, 5.2 Hz, 1H, Z—CH$_2$), 3.74 (t, J=5.8 Hz, 1H, Z—CH$_2$—N). $^{13}$C NMR (DMSO) δ 176.9, 166.8, 134.2, 133.3, 132.1, 130.8, 130.0, 129.4, 129.2, 129.1, 128.4, 127.0, 127.0, 122.1, 62.3 (E-CH$_2$—N), 59.3 (Z—CH$_2$—N), 48.1 (Z—CH$_2$), 44.5 (E-CH$_2$). MS (ESI+): 348 [M-Br]. Anal. (C$_{20}$H$_{18}$BrN$_3$OS) C, H, Br, N, S. Calculated: C, 56.08%; H, 4.24%; N, 9.81%; S, 7.49%; Br, 18.65%. Found: C, 55.79%; H, 4.08%; N, 9.62%; S, 7.33%; Br, 18.42%.

3-(1-Naphthyl)-2-phenyl-5-(3-pyridylmethylimino)-2,5-dihydro-1,2,4-thiadiazole dihydrobromide (VP2.32)

Imidoylthiourea VP2.27 (0.600 g, 1.52 mmol), bromine (0.155 ml, 3.03 mmol). Reaction time: 24 h. Grey solid (540 mg, 64%) mp 177-178° C. $^1$H NMR (DMSO) δ 10.56 (s, 1H), 8.87 (m 1H), 8.83 (d, J=5.0 Hz, 1H), 8.41 (d, J=7.8 Hz, 1H), 8.06 (d, J=8.1 Hz, 1H), 7.95 (m, 4H), 7.69-7.25 (m, 8H), 5.08 (d, J=5.0 Hz, 2H). $^{13}$C NMR (DMSO) δ 176.9, 165.4, 145.1, 144.1, 142.1, 141.7, 138.9, 135.4, 133.9, 132.7, 130.4, 129.8, 128.4, 127.6, 126.9, 125.1, 124.3, 123.9, 121.6, 45.1. MS (ESI+): 395[M–HBr$_2$]. Anal. (C$_{24}$H$_{20}$Br$_2$N$_4$S) C, H, Br, N, S. Calculated: C, 51.82%; H, 3.62%; N, 10.07%; S, 5.76%; Br, 28.73%. Found: C, 52.01%; H, 3.90%; N, 10.21%; S, 5.43%; Br, 28.55%.

5-(2-Hydroxyethylimino)-3-(1-naphthyl)-2-phenyl-2,5-dihydro-1,2,4-thiadiazole hydrobromide (VP2.33)

Imidoylthiourea VP2.28 (0.600 g, 1.72 mmol), bromine (0.176 ml, 3.44 mmol). Reaction time: 24 h. White solid (147 mg, 20%) mp 163-164° C. $^1$H NMR (DMSO) δ 10.21 (t, J=5.3 Hz, 1H), 8.08 (m, 2H), 7.97 (m, 2H), 7.78-7.65 (m, 1H), 7.68-7.15 (m, 7H), 3.74 (m, 2H), 3.65 (t, J=4.9 Hz, 2H), 3.49 (s, 1H). $^{13}$C NMR (DMSO) δ 177.0, 166.5, 134.6, 133.4, 132.7, 131.0, 130.5, 130.4, 130.2, 129.1, 128.4, 127.8, 127.6, 125.7, 125.5, 124.8, 59.5, 48.2. MS (ESI+): 348 [M-Br]. Anal. (C$_{20}$H$_{18}$BrN$_3$OS) C, H, Br, N, S. Calculated: C, 56.08%; H, 4.24%; N, 9.81%; S, 7.49%; Br, 18.65%. Found: C, 55.83%; H, 4.51%; N, 9.74%; S, 7.43%; Br, 18.45%.

3-Methyl-2-phenyl-5-(3-pyridylmethylimino)-2,5-dihydro-1,2,4-thiadiazole dihydrobromide (VP2.63)

Imidoylthiourea VP2.58 (1.00 g, 3.52 mmol), bromine (0.362 ml, 7.04 mmol). Reaction time: 2 h. White solid (390 mg, 25%) mp 109-110° C. $^1$H NMR (DMSO) δ 10.36 (s, 1H), 9.00 (s, 1H), 8.89 (d, J=5.0 Hz, 1H), 8.58 (d, J=8.0 Hz, 1H), 8.03 (m, 1H), 7.58 (m, 5H), 5.09 (d, J=5.6 Hz, 2H), 2.35 (s, 3H). $^{13}$C NMR (DMSO) δ 176.3, 168.2, 143.2, 143.0, 135.9, 133.5, 133.2, 131.0, 130.2, 127.2, 126.4, 44.7, 16.3. MS (ESI+): 283[M–HBr$_2$]. Anal. (C$_{15}$H$_{16}$Br$_2$N$_4$S) C, H, Br, N, S. Calculated: C, 40.56%; H, 3.63%; N, 12.61%; S, 7.22%; Br, 35.98%. Found: C, 40.38%; H, 3.61%; N, 12.59%; S, 7.20%; Br, 35.58%.

5-(2-Morpholinethylimino)-2,3-diphenyl-2,5-dihydro-1,2,4-thiadiazole dihydrobromide (VP3.15)

Imidoylthiourea VP3.13 (0.60 g, 1.63 mmol), bromine (0.160 ml, 3.26 mmol). Reaction time: 3 h. White solid (438 mg, 51%) mp 241-242° C. $^1$H NMR (DMSO) δ 10.11 (s), 7.52-7.4 (m, 10H), 4.18 (m, 2H), 4.01 (m, 2H), 3.78-3.45 (m, 8H). $^{13}$C NMR (DMSO) δ 176.3, 164.4, 134.2, 133.1, 131.2, 130.8, 130.8, 129.3, 128.2, 126.25, 63.2, 54.3, 52.0, 38.9. $^{15}$N NMR (DMSO) δ 252, 212, 130, 16. MS (ESI+): 367[M–HBr$_2$]. Anal. (C$_{20}$H$_{24}$Br$_2$N$_4$OS) C, H, Br, N, S. Calculated: C, 45.47%; H, 4.58%; N, 10.61%; S, 6.07%; Br, 30.25%. Found: C, 45.23%; H, 4.51%; N, 10.65%; S, 6.39%; Br, 30.59%.

General Procedure for Hydrochloride Iminothiadiazole Synthesis

[Chetia, J. P., Mazumder, M. P., Mahajan, M. P. "One-Pot synthesis of 2-aryl-3-phenyl(benzyl)-5-phenylimino-1,2,4-thiadiazolines using N-chlorosuccinimide". Synthesis 1995, 83-84]

To the corresponding thiourea (1 equiv.) in CH2Cl2 N-chlorosuccinimide (1.1 equiv) was added. The mixture was stirred for 2 h at room temperature. Then water (200 mL) and AcOEt (200 mL) were added. The organic layer was washed with water, dried over MgSO$_4$ and the solvent was removed under reduced pressure. The product was recrystallized from MeOH/H$_2$O.

5-(2-Hydroxyethylimino)-2,3-diphenyl-2,5-dihidro-1,2,4-thiadiazole hydrochloride (VP2.3)

Imidoylthiourea VP1.12 (0.600 g, 2.00 mmol), N-chlorosuccinimide (0.290 g, 2.20 mmol). Reaction time: 2 h. White solid (320 mg, 48%) mp 177-179° C. $^1$H NMR (DMSO) δ 10.57 (t, J=5.6 Hz, 1H), 7.68-7.17 (m, 10H), 5.00 (bs, 1H), 3.77 (q, J=5.5 Hz, 2H), 3.66 (t, J=5.5, 2H). $^{13}$C NMR (DMSO) δ 176.7, 165.3, 135.3, 133.1, 131.2, 130.8, 130.8, 129.3, 128.2, 127.6, 59.6, 48.1. $^{15}$N NMR (DMSO) δ 131, 201, 247. MS (ESI+): 298[M-Cl]. Anal. (C$_{16}$H$_{16}$ClN$_3$OS) C, H, Cl, N, S. Calculated: C, 57.56%; H, 4.83%; N, 12.59%; S, 9.61%; Cl, 10.62%. Found: C, 57.28%; H, 4.95%; N, 12.62%; S, 9.39%; Cl, 10.27%.

3-(1-Naphthyl)-2-phenyl-5-(3-pyridylmethylimino)-2,5-dihydro-1,2,4-thiadiazole hydrochloride (VP3.7)

Imidoylthiourea VP2.27 (0.600 g, 1.51 mmol), N-chlorosuccinimide (0.22 g, 1.66 mmol). Reaction time: 1 h. White solid (208 mg, 32%) mp 204-205° C. $^1$H NMR (DMSO) δ 11.03 (s, 1H), 8.66 (m, 1H), 8.55 (m, 1H), 8.0-7.4 (m, 14H), 4.94 (s, 2H). $^{13}$C NMR (DMSO) δ 176.8, 165.3, 144.6, 135.3, 133.1, 131.2, 130.8, 130.8, 129.3, 128.2, 127.6, 44.1. MS (ESI+): 395[M-Cl]. Anal. (C$_{25}$H$_{20}$ClN$_4$S) C, H, Cl, N, S. Calculated: C, 66.89%; H, 4.44%; N, 13.00%; S, 7.44%; Cl, 8.23%. Found: C, 66.73%; H, 4.72%; N, 12.85%; S, 7.39%; Cl, 8.60%.

3-(4-Methoxyphenyl)-5-pentylimino-2-phenyl-2,5-dihydro-1,2,4-thiadiazole hydrochloride (VP3.9)

Imidoylthiourea VP1.38 (0.600 g, 1.69 mmol), N-chlorosuccinimide (0.25 g, 1.85 mmol). Reaction time: 2 h. Pale yellow solid (185 mg, 28%) mp 138-139° C. $^1$H NMR (DMSO) δ 10.60 (t, J=5.2, 1H), 7.62-7.5 (m, 5H), 7.4 (d, J=8.3 Hz, 2H), 6.8 (d, J=8.3 Hz, 2H), 3.78 (s, 3H), 3.71 (m, 2H), 1.71 (m, 2H), 1.42-1.32 (m, 4H), 0.91 (t, J=7.2 Hz, 3H). $^{13}$C NMR (DMSO) δ 175.4, 164.7, 162.8, 135.3, 133.1, 131.2, 130.8, 130.8, 129.3, 128.2, 127.6, 119.3, 114.5, 56.0, 44.9, 28.7, 28.4, 22.0, 14.2. MS (ESI+): 354[M-Cl]. Anal. (C$_{20}$H$_{24}$ClN$_3$OS) C, H, Cl, N, S. Calculated: C, 61.60%; H, 6.20%; N, 10.78%; S, 8.22%; Cl, 9.09%. Found: C, 61.47%; H, 6.16%; N, 10.65%; S, 8.39%; Cl, 9.42%.

General Procedure for Iminothiadiazole Synthesis

[Chetia, J. P., Mazumder, M. P., Mahajan, M. P. "One-Pot synthesis of 2-aryl-3-phenyl(benzyl)-5-phenylimino-1,2,4-thiadiazolines using N-chlorosuccinimide". Synthesis 1995, 83-84]

To the corresponding thiourea (1 equiv) in CH$_2$Cl$_2$ N-chlorosuccinimide (1.1 equiv) was added. The mixture was stirred for 2 h at room temperature. Then water (200 mL) and AcOEt (200 mL) were added. The organic layer was washed with a NaHCO$_3$ saturated solution, dried over MgSO$_4$ and the solvent was removed under reduced pressure. The product was recrystallized from MeOH/H$_2$O.

2,3-Diphenyl-5-phenylimino-2,5-dihydro-1,2,4-thiadiazole (VP1.23-b)

Imidoylthiourea VP1.20 (0.41 g, 1.24 mmol), N-chlorosuccinimide (0.18 g, 1.36 mmol). Reaction time: 2 h. Yellow solid (131 mg, 32%) mp 143-144° C. (lit.[20] 141-142° C.). $^1$H NMR (DMSO) δ 7.93-7.61 (m, 2H), 7.63-7.27 (m, 11H), 7.23-6.55 (m, 2H). $^{13}$C NMR (DMSO) δ 167.5, 160.6, 159.6, 139.4, 136.7, 136.2, 134.4, 129.7, 129.1, 128.6, 128.5, 128.0, 127.2, 126.1, 125.7, 125.1, 124.6, 122.4, 121.5, 120.6, 120.4. MS (ESI+): 330 [M+H]. Anal. (C$_{20}$H$_{15}$N$_3$S) C, H, N, S. Calculated: C, 72.42%; H, 4.59%; N, 12.76%; S, 9.73%. Found: C, 72.02%; H, 4.59%; N, 12.68%; S, 9.73%; Cl, 10.27%.

5-Ethoxycarboximethylimino-2,3-diphenyl-2,5-dihydro-1,2,4-thiadiazole (VP1.45)

Imidoylthiourea VP1.13 (0.50 g, 1.46 mmol), N-chlorosuccinimide (0.22 g, 1.61 mmol). Reaction time: 2 h. Orange solid (321 mg, 65%) mp 151-152° C. $^1$H NMR (DMSO) δ 8.11-7.93 (m, 2H), 7.72-6.89 (m, 8H), 5.36 (s, 2H, CH$_2$—N=), 4.42-4.17 (m, 1H, E-CH$_2$), 4.13 (q, J=7.1 Hz, 1H, Z—CH$_2$), 1.47-1.17 (m, 1.5H E-CH$_3$), 1.20-0.81 (m, 1.5H, Z—CH$_3$). $^{13}$C NMR (DMSO) δ 168.9, 167.3, 161.6, 161.2, 148.2, 136.1, 134.9, 132.4, 130.2, 129.1, 127.9, 126.7, 119.5, 62.0 (E-CH$_2$), 59.8 (Z—CH$_2$), 46.8 (CH$_2$), 14.4 (CH$_3$). MS (ESI+): 340 [M+H]. Anal. (C$_{18}$H$_{17}$N$_3$O$_2$S) C, H, N, S. Calculated: C, 63.70%; H, 5.05%; N, 12.38%; S, 9.45%. Found: C, 63.45%; H, 4.89%; N, 12.11%; S, 9.54%.

Determination of PDE7 Inhibition

PDE-7 inhibition was performed with a commercial kit for the determination of phosphodiesterase activity (GE Healthcare Life Sciences, cat#TRKQ7090).

The compounds to be evaluated were incubated (in concentrations between 0.1 nM and 100 μM) in presence of 0.02 U/well of PDE7A1 (Calbiochem cat#524751) and 0.05 μCi of [$^3$H] cAMP, for 20 min at 30° C. in the assay buffer of kit (total volume=100 μl).

After this time, 50 μl of a suspension of 20 mg/ml microspheres of SPA of Ytrium silicate were added and was maintained under stirring at room temperature for 60 min. Finally, the plate was settled for 20 min and radioactivity was detected in a Microbeta Trilux reader.

In every assay there were included two points without PDE7A1 (blank) and two points with PDE7A1 without inhibitors (control).

Data Analysis: All the compounds were evaluated firstly at the concentration of 10 µM and the percentage of PDE7A1 inhibition was calculated, according to the following formula (cpm=counts per minute):

% Inhibition=((cpm control−cpm sample)×100)/(cpm control−cpm blank assay).

For those compounds with % inhibition values above 45% it was calculated its inhibitory potency ($IC_{50}$) building the dose-response curve.

The data were adjusted with the software Prism v 2.1 (GraphPad Software) using the non lineal fitting.

TABLE 1

$IC_{50}$ of 1,2,4-thiadiazoles-5-imino substituted as hydrobromides.

| $R^1$ | $R^2$ | $R^3$ | $IC_{50}$ (PDE7A) |
|---|---|---|---|
| Ph | Ph | H | 1.02 µM |
| Ph | Ph | n-Pent | 1.44 µM |
| Ph | Ph | Cy | 1.64 µM |
| Ph | Ph | $CH_2Pyr$ | 0.38 µM |
| Ph | Ph | $CH_2CO_2Et$ | 1.13 µM |
| Ph | Ph | $(CH_2)_2OH$ | 1.11 µM |
| pOMePh | Ph | $CH_2Pyr$ | 0.86 µM |
| pOMePh | Ph | $(CH_2)_2OH$ | 1.50 µM |
| pOMePh | Ph | Ph | 4.36 µM |
| pOMePh | Ph | $CH_2CO_2Et$ | 0.89 µM |
| pOMePh | Ph | n-Pent | 0.81 µM |
| Ph | pOMePh | $CH_2Pyr$ | 0.85 µM |
| Ph | pOMePh | $(CH_2)_2OH$ | 1.18 µM |
| Ph | pOMePh | $CH_2CO_2Et$ | 0.78 µM |
| Ph | Ph | Ph | 3.03 µM |
| Ph | $4-NO_2$—Ph | $CH_2Py$ | 0.84 µM |
| Ph | $4-NO_2$—Ph | $CH_2CO_2Et$ | 0.79 µM |
| $4-CF_3$—Ph | Ph | $CH_2Py$ | 87%@10 µM |
| Ph | 1-Naph | $CH_2Py$ | 0.87 µM |
| Ph | 1-Naph | $CH_2CH_2OH$ | 2.20 µM |
| 1-Naph | Ph | $CH_2Py$ | 1.08 µM |
| 1-Naph | Ph | $CH_2CH_2OH$ | 1.24 µM |
| Me | Ph | $CH_2Py$ | 54%@10 µM |
| Ph | Ph | Morph-$(CH_2)_2$ | 1.59 µM |

TABLE 2

$IC_{50}$ of 1,2,4-thiadiazoles-5-imino substituted as hydrochlorides.

| $R^1$ | $R^2$ | $R^3$ | $IC_{50}$ (PDE7A) |
|---|---|---|---|
| Ph | Ph | $CH_2CH_2OH$ | 1.97 µM |
| 1-Naph | Ph | $CH_2Py$ | 1.50 µM |
| 4-OMe—Ph | Ph | n-Pent | 3.70 µM |

TABLE 3

$IC_{50}$ of 1,2,4-thiadiazoles-5-imino substituted as free bases.

| $R^1$ | $R^2$ | $R^3$ | $IC_{50}$ (PDE7A) |
|---|---|---|---|
| Ph | Ph | Ph | 3.52 µM |
| Ph | Ph | $CH_2CO_2Et$ | 6%@10 µM |

Measurement of the Neuroprotective Effect of the 1,2,4-Thiadiazoles-5-Imino Substituted Derivatives in Microglia Primary Cultures Primary cultures of microglia were used [Luna-Medina, R.; Cortes-Canteli, M.; Alonso, M.; Santos, A.; Martinez, A.; Perez-Castillo, A., Regulation of inflammatory response in neural cells in vitro by thiadiazolidinones derivatives through peroxisome proliferator-activated receptor gamma activation. J. Biol. Chem. 2005, 280, 21453-21462]. The primary cultures of microglia were obtained from the cortex and hippocampus of postnatal 2-day-old mice. After dissecting the cortex and hippocampus and clearing them of the meninges, cells are disintegrated by mechanical grinding and incubated with 0.25% trypsin/EDTA at 37° C. during 45 minutes. DMEM with 10% foetal serum is added to stop the digestion with trypsin and mechanical grinding of the tissue is completed. Centrifugation is applied at 800×g/5 min and the precipitate washed 3 times in EBSS; finally, cells are resuspended in DMEM plus 10% foetal serum and seeded at a density of $0.5×10^5$ cells/$cm^2$. Cells are incubated for 10-12 days after which a monolayer of astrocytes is observed to which microglia cells lightly adhere. To isolate microglia cells culture bottles are incubated in a rotary agitator at 37° C. during 4 hours at 250 rpm and the medium containing microglia centrifuged at 1500×g/5 10 min. Microglia cells are resuspended in DMEM/10% FBS and seeded at a density of $2-4×10^5$ cells/$cm^2$. After 1 hour of incubation, to allow them to adhere to the plate, they are washed with TD and incubated in DMEM/10% FBS during 24 hours, after which cells are used in the various experiments. The level of purity of these cultures is determined by immunocytochemistry assays with 15 neuron-specific antibodies (6-tubulin and MAP2), astrocytes (GFAP), oligodendrocytes (CNPase) and microglia (OX42).

Figure 1:
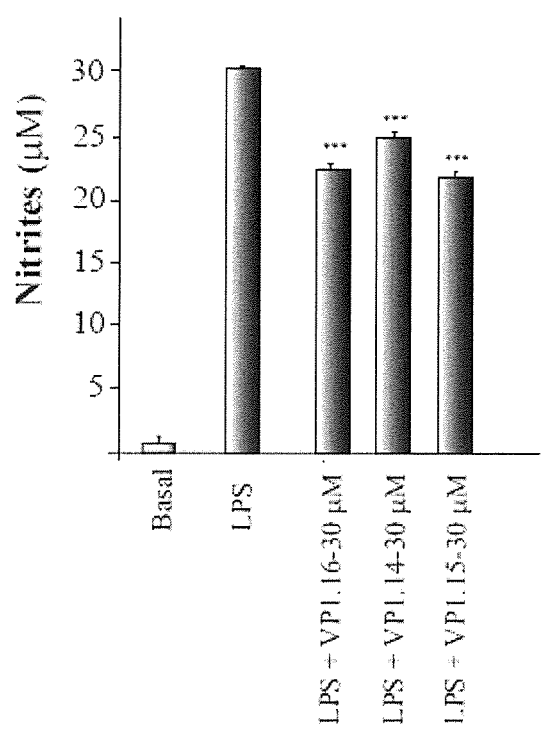
Figure 2:
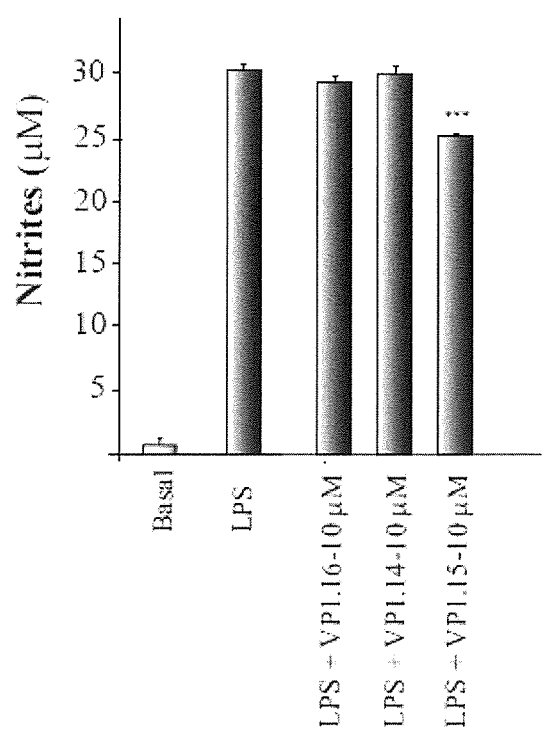
Figure 3:
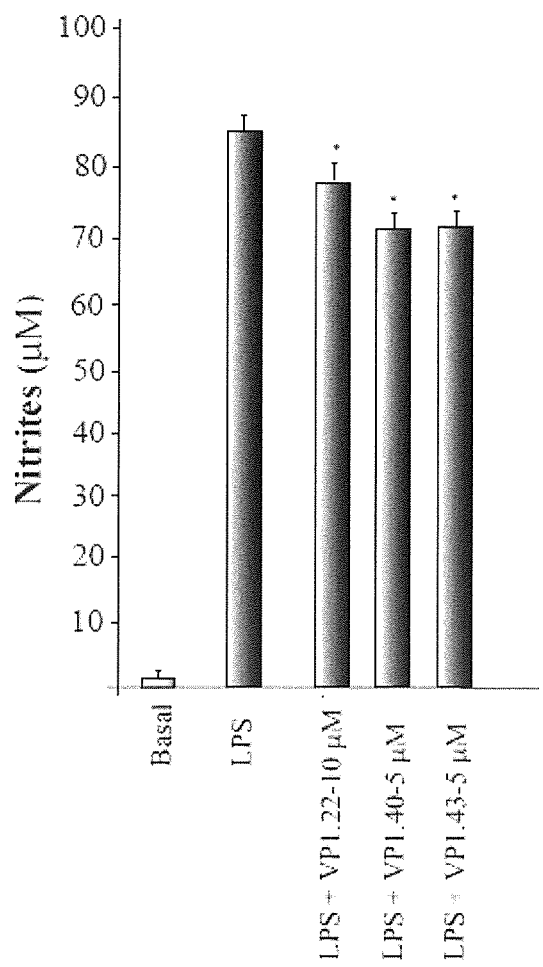

Cell cultures of microglia are treated with LPS (10 µg/ml) in the absence and presence of the different compounds. The compounds are added 1 hour before the inflammatory stimulus. At different times after incubation, cells are washed and gathered for corresponding measurement of the effect of the compounds on NO (nitric oxide) production by iNOS (inducible nitric oxide synthase) as an indicator of neural damage due to inflammatory processes [Kroncke K. D.; Fehsel K.; Kolb-Bachofen V., Nitric oxide: cytotoxicity versus cytoprotection—how, why, when, and where? *Nitric Oxide* 1997, 1, 107-120]. To this effect, after 24 hours of incubation the quantity of nitrites, one of the oxidation products of NO, is determined. To achieve this, the method based on the Griess reaction is used [Griess, P. Bemerkungen zu der abhandlung der H. H. Weselsky and Benedikt Ueber einige azoverbindungen. *Chem. Ber.* 1879, 12, 426-428]: 100 µl of supernatant from the cultures is mixed with 100 µl of 30 Griess reagent in a 96-well plate and incubated during 15 min at room temperature. Next, absorbance is measured at 540 nm in a microplate reader. The amount of nitrites produced is determined using a standard sodium nitrite curve. (FIGS. 1 to 3).

Measurement of the Neuroprotective Effect of the 1,2,4-Thiadiazoles-5-Imino Substituted Derivatives in Astroglia Primary Cultures Glial cells were prepared from neonatal rat cerebral cortex, as previously described [Luna-Medina, R.; Cortes-Canteli, M.; Alonso, M.; Santos, A.; Martinez, A.; Perez-Castillo, A., Regulation of inflammatory response in neural cells in vitro by thiadiazolidinones derivatives through peroxisome proliferator-activated receptor gamma activation. J. Biol. Chem. 2005, 280, 21453-21462]. Briefly, after removal of the meninges the cerebral cortex was dissected, dissociated, and incubated with 0.25% trypsin/EDTA at 37° C. for 1 hour. After centrifugation, the pellet was washed 3 times with HBSS (Gibco) and the cells were placed on non-coated flasks and maintained in HAMS/DMEM (1:1) medium containing 10% FBS. After 15 days the flasks were agitated on an orbital shaker for 4 hours at 240 rpm at 37° C., the supernatant was collected, centrifuged, and the cellular pellet containing the microglial cells resuspended in complete medium (HAMS/DMEM (1:1) containing 10% FBS) and seeded on uncoated 96-well plates. Cells were allowed to adhere for 2 hours and the medium was removed to eliminate non-adherent oligodendrocytes. New fresh medium containing 10 ng/mL of GM-CSF was added. The remaining astroglial cells adhered on the flasks were then trypsinized, collected, centrifugated and plated onto 96-well plates with complete medium. The purity of cultures obtained by this procedure was >98% as determined by immunofluorescence with the OX42 (microglial marker) and the GFAP (astroglial marker) antibodies. After 1 week in culture, cells were treated with different compounds at several concentrations. Cell viability was then measured after 16 h in culture. For nitrite release quantification some cultures were also treated with LPS (10 μg/mL) alone or in combination with compounds (FIG. 5).

Measurement of the Blood Brain Permeability of the Compounds (CNS Using Parallel Artificial Membranes (PAMPA)

Prediction of permeability of the compounds in the CNS, ability to cross the blood-brain barrier (BBB), was evaluated using a parallel artificial membrane permeability assay (PAMPA) [Di, L.; kerns, E. H.; Fan, K.; McConnell, O. J.; Carter, G. T. "High throughput artificial membrane permeability assay for blood-brain barrier" *Eur. J. Med. Chem.*, 2003, 38 (3), 223-232]. Ten commercial reference drugs, phosphate buffer saline solution at pH 7.4 (PBS), DMSO and dodecane were purchased from Sigma, Acros organics, Aldrich and Fluka. The porcine polar brain lipid (PBL) (catalog no. 141101) was from Avanti Polar Lipids. The donor plate was a 96-well filtrate plate (Multiscreen® IP Sterile Plate PDVF membrane, pore size is 0.45 μM, catalog no. MAIPS4510) and the acceptor plate was an indented 96-well plate (Multiscreen®, catalog no. MAMCS9610) both from Millipore. Filter PDVF membrane units (diameter 30 mm, pore size 0.45 μm) from Symta were used to filtered the samples. A 96-well plate UV reader (Thermoscientific, Multiskan spectrum) was used for the UV measurements. Test compounds, which ability to cross the BBB is well-known, [(3-5 mg of Cafeine, Enoxacine, Hydrocortisone, Desipramine, Ofloxacine, Piroxicam, Testosterone), (12 mg of Promazine) and 25 mg of Verapamile and Atenolol] were dissolved in DMSO (250 μL). 25 microliters of this compound stock solution was taken and 225 μL of DMSO and 4750 μL of PBS pH 7.4 buffer were added to reach 5% of DMSO concentration in the experiment. These solutions were filtered. The acceptor 96-well microplate was filled with 180 μL of PBS:DMSO (95:5). The donor 96-well plate was coated with 4 μL of porcine brain lipid in dodecane (20 mg mL$^{-1}$) and after 5 minutes, 180 μL of each compound solution was added. 1-2 mg of every compound to be determined their ability to pass the BBB were dissolved in 250 μL of DMSO and 4750 μL of PBS pH 7.4 buffer, filtered and then added to the donor 96-well plate. Then the donor plate was carefully put on the acceptor plate to form a "sandwich", which was left undisturbed for 4 h at 25° C.

During this time the compounds diffused from the donor plate through the brain lipid membrane into the acceptor plate. After incubation, the donor plate was removed. The concentration of compounds and commercial drugs in the acceptor and the donor wells was determined by UV plate reader. Every sample was analyzed from three to five wavelengths, in 3 wells and in at least three independent runs. Results are given as the mean [standard deviation (SD)] and the average of the three runs is reported. 11 quality control compounds (previously mentioned) of known BBB permeability were included in each experiment to validate the analysis set.

The results are listed in Table 4 where can be viewed as the vast majority of the compounds are capable of penetrating the BBB.

TABLE 4

Permeability (Pe 10$^{-6}$ cm s$^{-1}$) in the PAMPA-BBB assay for 11 commercial drugs (used in the experiment validation) and different compounds here presented with their predictive penetration in the CNS.[a]

| Compound | Lit. | Pe (10$^{-6}$ cm s$^{-1}$)[a] | Prediction |
|---|---|---|---|
| Atenolol | 0.8 | 0.8 ± 1.1 | |
| Cafeine | 1.3 | 1.5 ± 0.3 | |
| Desipramine | 12 | 15.1 ± 1.1 | |
| Enoxacin | 0.9 | 0.9 ± 0.5 | |
| Hidrocortisone | 1.9 | 2.7 ± 0.4 | |
| Imipramine | 13 | 10.7 ± 1.5 | |
| Ofloxacin | 0.8 | 1.1 ± 0.3 | |
| Piroxicam | 2.5 | 2.2 ± 0.9 | |
| Promazine | 8.8 | 9.7 ± 1.5 | |
| Testosterone | 17 | 15.4 ± 0.5 | |
| Verapamil | 16 | 15.3 ± 1.5 | |
| VP-1.14 | | 10.7 ± 0.3 | CNS+ |
| VP-1.15 | | 15.4 ± 2.0 | CNS+ |
| VP-1.16 | | 6.2 ± 0.4 | CNS+ |
| VP-1.21 | | 11.0 ± 1.6 | CNS+ |
| VP-1.40 | | 13.7 ± 0.8 | CNS+ |
| VP-1.43 | | 4.4 ± 0.6 | CNS+ |
| VP-1.60 | | 6.2 ± 0.4 | CNS+ |
| VP-1.61 | | 13.7 ± 1.0 | CNS+ |
| VP-1.62 | | 4.0 ± 0.8 | CNS+/CNS− |
| VP-1.65 | | 3.8 ± 0.2 | CNS+/CNS− |
| VP-2.3 | | 15.0 ± 2.0 | CNS+ |
| VP-2.33 | | 10.2 ± 0.6 | CNS+ |
| VP-2.63 | | 5.3 ± 0.9 | CNS+ |

PBS:DMSO (95:5) using as solvent.
[a]Data determination ± standard deviation of at least 3 independent experiments.

The invention claimed is:

1. A method for inhibiting phosphodiesterase (PDE7) activity comprising the administration to a patient in need thereof a therapeutically effective amount of a compound of formula (II):

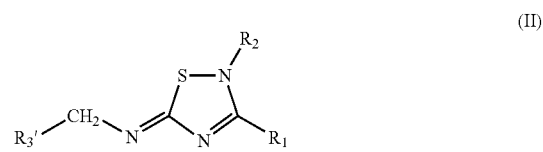

Wherein:

$R_1$ is a group $X_1$—$R_1'$ wherein $X_1$ is a single bond;

$R_1'$ is $C_1$-$C_6$ alkyl, aryl, $R_1'$ being optionally substituted with one or more groups $X_1'$—$R_8$ which may be identical or different;

$X_1'$ is a single bond or a group selected from $C_1$-$C_6$ alkylene, $X_1'$ being optionally substituted with at least one or more groups which may be identical or different and are selected from F, Cl, Br, I;

$R_8$ is H, —OH, =O, —NO$_2$, CN, F, Cl, Br, I, $C_1$-$C_4$ alkyl, —CO$_2$R$_{6a}$, —C(=O)R$_{6a}$, C(=S)R$_{6a}$, SO$_2$R$_{6a}$, SOR$_{6a}$, SO$_3$R$_{6a}$, SR$_{6a}$, OR$_{6a}$, C(=O)NR$_{6a}$R$_{7a}$, C(=S)NR$_{6a}$R$_{7a}$, C(=N—CN)NR$_{6a}$R$_{7a}$, C(=N—SO$_2$NH$_2$)NR$_{6a}$R$_{7a}$, C(=CH—NO$_2$)NR$_{6a}$R$_{7a}$, SO$_2$NR$_{6a}$R$_{7a}$, C(=NR$_{6a}$)NHR$_{7a}$, C(=NR$_{6a}$)R$_{7a}$ or NR$_{6a}$R$_{7a}$, R$_{6a}$ and R$_{7a}$ being independently selected from R$_4$ and R$_5$;

R₂ is aryl, R₂ being optionally substituted with at least one or more groups which may be identical or different and are selected from —NO₂, OR$_{6b}$, R$_{6b}$ being independently selected from R₄ and R₅;

R₃' is selected from pyridyl, —(CH₂)$_n$—(C₅-C₇-heterocycloalkyl), (CH₂)$_n$—OR₁₂ or —(CH₂)$_n$—C(O)OR₁₂, n is a number between 0 and 20;

R₁₂ is independently selected from the groups defined for R₁₀;

R₄ and R₅ are independently selected from: C₁-C₆ alkyl; and

R₁₀ is independently selected from H and C₁-C₆ alkyl;

or a pharmaceutically acceptable salt thereof.

2. The method according to claim 1 wherein the patient in need thereof is affected by an inflammatory or autoimmune pathology, and inhibiting PDE7 activity affects the inflammatory or autoimmune pathology.

3. The method according to claim 2, wherein the inflammatory and/or autoimmune pathology is a pathology selected from the group consisting of: inflammatory bowel disease, inflammatory joint diseases, atopic dermatitis and other inflammatory dermatological diseases, neuritis, encephalitis, encephalomyelitis, multiple sclerosis or peripheral nervous system, myositis, vasculitis, systemic lupus erythematosus, asthma, chronic obstructive pulmonary disease, infectious diseases that occur with inflammation, graft rejection, conjunctivitis and inflammatory eye diseases, otitis and mucositis.

4. The method according to claim 1 wherein the patient in need thereof is affected by a neurodegenerative or neurological pathology, and inhibiting PDE7 activity affects the neurodegenerative or neurological pathology.

5. The method according to claim 4, wherein the neurodegenerative or neurological pathology is selected from the group consisting of: Alzheimer's disease, Parkinson's disease, amyotrophic lateral sclerosis, cerebral ischemia, post-encephalic parkinsonisms, dystonias, Tourette's syndrome, periodic limbic movement disorders, restless leg syndrome and attention deficit hyperactivity disorder.

6. The method according to claim 1 wherein the patient in need thereof is affected by movement alterations, and inhibiting PDE7 activity affects the movement alterations.

7. The method according to claim 1 wherein the compound of formula (II) is in the form of a pharmaceutically acceptable salt selected from the group consisting of: hydrobromide and hydrochloride salts thereof.

8. A method for inhibiting phosphodiesterase 7 (PDE7) activity in a patient in need thereof, said method comprising administering to said patient a therapeutically effective amount of a compound of the formula (II):

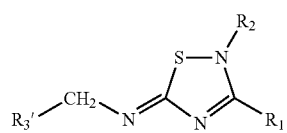

(II)

Wherein:

R₁ is phenyl or naphthyl each of which is optionally substituted by one or more substituents independently selected from the group consisting of F, Cl, Br, I, OH, CN, CF₃, NO₂, C$_{1-6}$-alkyl and C$_{1-6}$-alkoxy;

R₂ is phenyl or naphthyl each of which is optionally substituted by one or more substituents independently selected from the group consisting of F, Cl, Br, I, OH, CN, CF₃, NO₂, C$_{1-6}$-alkyl and C$_{1-6}$-alkoxy;

R₃' is selected from pyridyl, —(CH₂)$_n$—(C₅-C₇-heterocycloalkyl), —(CH₂)$_n$—OR₁₂ or —(CH₂)$_n$—C(O)OR₁₂;

n is 0-6; and

R₁₂ is H or C$_{1-6}$-alkyl;

or a pharmaceutically acceptable salt thereof.

9. The compound according to claim 8 wherein R₃' is pyridyl.

10. The compound according to claim 9 wherein it is selected from the group consisting of:
2,3-Diphenyl-5-(3-pyridylmethylimino)-2,5-dihydro-1,2,4-thiadiazole;
3-(4-Methoxyphenyl)-2-phenyl-5-(3-pyridylmethylimino)-2,5-dihydro-1,2,4-thiadiazole;
2-(4-Methoxyphenyl)-3-phenyl-5-(3-pyridylmethylimino)-2,5-dihydro-1,2,4-thiadiazole;
2-(4-Nitrophenyl)-3-phenyl-5-(3-pyridylmethylimino)-2,5-dihydro-1,2,4-thiadiazole;
2-Phenyl-5-(3-pyridylmethylimino)-3-(4-trifluoromethylphenyl)-2,5-dihydro-1,2,4-thiadiazole;
2-(1-Naphthyl)-3-phenyl-5-(3-pyridylmethylimino)-2,5-dihydro-1,2,4-thiadiazole;
3-(1-Naphthyl)-2-phenyl-5-(3-pyridylmethylimino)-2,5-dihydro-1,2,4-thiadiazole; and
3-Methyl-2-phenyl-5-(3-pyridylmethylimino)-2,5-dihydro-1,2,4-thiadiazole.

11. The compound according to claim 8 wherein R₃' is —C(O)OR₁₂.

12. The compound according to the claim 11 wherein it is selected from the group consisting of:
5-Ethoxycarbonylmethylimino-2,3-diphenyl-2,5-dihydro-1,2,4-thiadiazole;
5-Ethoxycarbonylmethylimino-3-(4-methoxyphenyl)-2-phenyl-2,5-dihydro-1,2,4-thiadiazole;
5-Ethoxycarbonylmethylimino-2-(4-methoxyphenyl)-3-phenyl-2,5-dihydro-1,2,4-thiadiazole; and
5-Ethoxycarboxymethylimino-2-(4-nitrophenyl)-3-phenyl-2,5-dihydro-1,2,4-thiadiazole.

13. The compound according to claim 8 wherein R₃' is a group —(CH₂)$_n$—OR₁₂ with n being between 0 and 6, with the condition that R₃' cannot be (CH₂)₂—OH.

14. The compound according to claim 13 wherein it is selected from the group consisting of:
5-(2-Hydroxyethylimino)-2,3-diphenyl-2, 5-dihydro-1,2,4-thiadiazole;
5-(2-Hydroxyethylimino)-3-(4-methoxyphenyl)-2-phenyl-2, 5-dihydro-1,2,4-thiadiazole;
5-(2-Hydroxyethylimino)-2-(4-methoxyphenyl)-3-phenyl-2, 5-dihydro-1,2,4-thiadiazole;
5-(2-Hydroxyethylimino)-2-(1-naphthyl)-3-phenyl-2, 5-dihydro-1,2,4-thiadiazole; and
5-(2-Hydroxyethylimino)-3-(1-naphthyl)-2-phenyl-2, 5-dihydro-1,2,4-thiadiazole.

15. The compound according to claim 8 wherein R₃' is a group (CH₂)$_n$—(C₃-C₁₀ heterocycloalkyl) with n being between 0 and 6.

16. The compound according to claim 15 which is 5 (2-Morpholinethylimino)-2,3-diphenyl-2,5-dihydro-1,2,4-thiadiazole.

17. The method according to claim 3 wherein the inflammatory and/or autoimmune pathology is multiple sclerosis.

* * * * *